(12) United States Patent
McClure et al.

(10) Patent No.: US 6,214,870 B1
(45) Date of Patent: Apr. 10, 2001

(54) DIOXOCYCLOPENTYL HYDROXAMIC ACIDS

(75) Inventors: Kim F. McClure, Mystic; Ralph P. Robinson, Gales Ferry, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/536,950

(22) Filed: Mar. 28, 2000

Related U.S. Application Data

(60) Provisional application No. 60/127,071, filed on Mar. 31, 1999.

(51) Int. Cl.$^7$ .......................... A61K 31/36; C07D 317/44
(52) U.S. Cl. .......................... 514/466; 514/464; 514/465; 549/229; 549/436; 549/439; 549/441
(58) Field of Search .................................. 514/466, 464, 514/465; 549/229, 436, 439, 441

(56) References Cited

U.S. PATENT DOCUMENTS 5,672,615    9/1997    MacPherson et al. ................ 514/357

FOREIGN PATENT DOCUMENTS 9535276   12/1995   (WO) .......................... C07C/311/19
9833768    8/1998   (WO) .............................. G05D/1/03

OTHER PUBLICATIONS

Park, et al., J. Org. Chem., 63, pp. 113–117 (1998).

Primary Examiner—Ba K. Trinh
(74) Attorney, Agent, or Firm—Peter C. Richardson; Paul H. Ginsburg; Elsa Djuardi

(57) ABSTRACT

The present invention relates to dioxocyclopentyl hydroxamide derivatives of the formula

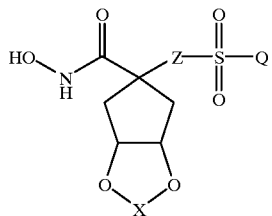

I wherein X, Z and Q are as defined in the specification, and to pharmaceutical compositions and methods of treatment thereof.

34 Claims, No Drawings

DIOXOCYCLOPENTYL HYDROXAMIC ACIDS

This application claims the benefit of U.S. Provisional No. 60/127,071, filed Mar. 31, 1999.

BACKGROUND OF THE INVENTION

The present invention relates to dioxocyclopentyl hydroxamide derivatives, and to pharmaceutical compositions comprising such derivatives and to the use of such derivatives in the treatment of arthritis, cancer and other diseases.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty-three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-$\alpha$, also known as cachectin). TNF-$\alpha$ is recognized to be involved in many infectious and autoimmune diseases (W. Friers, *FEBS Letters*, 285, 199 (1991)). Furthermore, it has been shown that TNF-$\alpha$ is the prime mediator of the inflammatory response seen in sepsis and septic shock (Spooner, et al., *Clinical Immunology and Immunopathology*, 62 S11 (1992)). There are two forms of TNF-$\alpha$, a type II membrane protein of relative molecular mass 26,000 (26 kD) and a soluble 17 kD form generated from the cell bound protein by specific proteolytic cleavage. The soluble 17 kD form of TNF-$\alpha$ is released by the cell and is associated with the deleterious effects of TNF-$\alpha$. This form of TNF-$\alpha$ is also capable of acting at sites distant from the site of synthesis. Thus, inhibitors of TACE prevent the formation of soluble TNF-$\alpha$ and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

The compounds of the invention are useful in the treatment of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, or septic shock.

The compounds of the present invention are also useful in the treatment of diseases in which inhibition of MMP's and/or ADAM's will provide therapeutic benefit, such as those characterized by matrix metalloproteinase or ADAM expression.

This invention also relates to a method of using the compounds of the invention in the treatment of the above diseases in mammals, especially humans, and to the pharmaceutical compositions useful therefore.

It is recognized that different combinations of MMP's and ADAM's are expressed in different pathological situations. Accordingly, inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to design inhibitors with differential metalloprotease activity. Specifically, for example, the inventors have been able to design molecules which selectively inhibit matrix metalloprotease-13 (MMP-13) preferentially over MMP-1.

SUMMARY OF THE INVENTION

The present invention relates to compounds of the formula

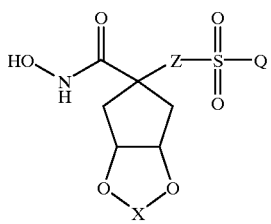

I wherein

X is >CR³R⁴ or >C=O;

Z is >CH₂ or >NR¹;

R¹ is hydrogen, ($C_1$–$C_6$)alkyl, ($C_6$–$C_{10}$)aryl($C_1$–$C_6$)alkyl, ($C_2$–$C_9$)heteroaryl($C_1$–$C_6$)alkyl or a group of the formula

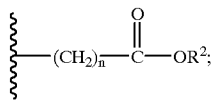

n is an integer from one to six;

R² is hydrogen or ($C_1$–$C_6$)alkyl;

R³ is hydrogen or ($C_1$–$C_6$)alkyl;

R⁴ is hydrogen, ($C_1$–$C_6$)alkyl, ($C_1$–$C_6$)alkoxy($C_1$–$C_6$) alkyl, ($C_6$–$C_{10}$)aryl, ($C_2$–$C_9$)heteroaryl, ($C_6$–$C_{10}$)aryl ($C_1$–$C_6$)alkyl, ($C_6$–$C_{10}$)aryl($C_6$–$C_{10}$)aryl, ($C_6$–$C_{10}$)aryl ($C_2$–$C_9$)heteroaryl, ($C_2$–$C_9$)heteroaryl($C_1$–$C_6$)alkyl, ($C_2$–$C_9$)heteroaryl($C_6$–$C_{10}$)aryl, ($C_2$–$C_9$)heteroaryl ($C_2$–$C_9$)heteroaryl, ($C_6$–$C_{10}$)aryloxy($C_1$–$C_6$)alkyl, ($C_6$–$C_{10}$)aryloxy($C_6$–$C_{10}$)aryl, ($C_6$–$C_{10}$)aryloxy ($C_2$–$C_9$)heteroaryl, ($C_2$–$C_9$)heteroaryloxy($C_1$–$C_6$) alkyl, ($C_2$–$C_9$)heteroaryloxy($C_6$–$C_{10}$)aryl, ($C_2$–$C_9$) heteroaryloxy($C_2$–$C_9$)heteroaryl, ($C_6$–$C_{10}$)aryl($C_1$–$C_6$) alkyl($C_6$–$C_{10}$)aryl, ($C_6$–$C_{10}$)aryl($C_1$–$C_6$)alkyl($C_2$–$C_9$) heteroaryl, ($C_6$–$C_{10}$)aryl($C_1$–$C_6$)alkoxy($C_6$–$C_{10}$)aryl, ($C_6$–$C_{10}$)aryl($C_1$–$C_6$)alkoxy($C_2$–$C_9$)heteroaryl, ($C_6$–$C_{10}$)aryloxy($C_1$–$C_6$)alkyl($C_6$–$C_{10}$)aryl, ($C_6$–$C_{10}$) aryloxy($C_1$–$C_6$)alkyl($C_2$–$C_9$)heteroaryl, ($C_2$–$C_9$) heteroaryl($C_1$–$C_6$)alkyl($C_6$–$C_{10}$)aryl, ($C_2$–$C_9$) heteroaryl($C_1$–$C_6$)alkyl($C_2$–$C_9$)heteroaryl, ($C_2$–$C_9$) heteroaryl($C_1$–$C_6$)alkoxy($C_6$–$C_{10}$)aryl, ($C_2$–$C_9$) heteroaryl($C_1$–$C_6$)alkoxy($C_2$–$C_9$)heteroaryl, ($C_2$–$C_9$) heteroaryloxy($C_1$–$C_6$)alkyl($C_6$–$C_{10}$)aryl, ($C_2$–$C_9$) heteroaryloxy($C_1$–$C_6$)alkyl($C_2$–$C_9$)heteroaryl, ($C_6$–$C_{10}$)aryl($C_6$–$C_{10}$)aryl($C_1$–$C_6$)alkyl or ($C_6$–$C_{10}$) aryl($C_1$–$C_6$)alkoxy($C_1$–$C_6$)alkyl, wherein each of said ($C_6$–$C_{10}$)aryl or ($C_2$–$C_9$)heteroaryl moieties is optionally substituted on any of the ring carbon atoms capable of forming an additional bond by one or more substituents per ring, independently selected from fluoro, chloro, bromo, ($C_1$–$C_6$)alkyl, ($C_1$–$C_6$)alkoxy, perfluoro ($C_1$–$C_3$)alkyl, perfluoro($C_1$–$C_3$)alkoxy and ($C_6$–$C_{10}$) aryloxy;

Q is ($C_1$–$C_6$)alkyl, ($C_6$–$C_{10}$)aryl, ($C_2$–$C_9$)heteroaryl, ($C_6$–$C_{10}$)aryl($C_1$–$C_6$)alkyl, ($C_6$–$C_{10}$)aryl($C_6$–$C_{10}$)aryl, ($C_6$–$C_{10}$)aryl($C_2$–$C_9$)heteroaryl, ($C_2$–$C_9$)heteroaryl ($C_1$–$C_6$)alkyl, ($C_2$–$C_9$)heteroaryl($C_6$–$C_{10}$)aryl, ($C_2$–$C_9$)heteroaryl($C_2$–$C_9$)heteroaryl, ($C_6$–$C_{10}$)aryloxy ($C_1$–$C_6$)alkyl, ($C_6$–$C_{10}$)aryloxy($C_6$–$C_{10}$)aryl, ($C_6$–$C_{10}$) aryloxy($C_2$–$C_9$)heteroaryl, ($C_2$–$C_9$)heteroaryloxy ($C_1$–$C_6$)alkyl, ($C_2$–$C_9$)heteroaryloxy($C_6$–$C_{10}$)aryl, ($C_2$–$C_9$)heteroaryloxy($C_2$–$C_9$)heteroaryl, ($C_6$–$C_{10}$)aryl ($C_1$–$C_6$)alkyl($C_6$–$C_{10}$)aryl, ($C_6$–$C_{10}$)aryl($C_1$–$C_6$)alkyl ($C_2$–$C_9$)heteroaryl, ($C_6$–$C_{10}$)aryl($C_1$–$C_6$)alkoxy ($C_6$–$C_{10}$)aryl, ($C_6$–$C_{10}$)aryl($C_1$–$C_6$)alkoxy($C_2$–$C_9$) heteroaryl, ($C_6$–$C_{10}$)aryloxy($C_1$–$C_6$)alkyl($C_6$–$C_{10}$)aryl, ($C_6$–$C_{10}$)aryloxy($C_1$–$C_6$)alkyl($C_2$–$C_9$)heteroaryl, ($C_2$–$C_9$)heteroaryl($C_1$–$C_6$)alkyl($C_6$–$C_{10}$)aryl, ($C_2$–$C_9$) heteroaryl($C_1$–$C_6$)alkyl($C_2$–$C_9$)heteroaryl, ($C_2$–$C_9$) heteroaryl($C_1$–$C_6$)alkoxy($C_6$–$C_{10}$)aryl, ($C_2$–$C_9$) heteroaryl($C_1$–$C_6$)alkoxy($C_2$–$C_9$)heteroaryl, ($C_2$–$C_9$) heteroaryloxy($C_1$–$C_6$)alkyl($C_6$–$C_{10}$)aryl, ($C_2$–$C_9$) heteroaryloxy($C_1$–$C_6$)alkyl($C_2$–$C_9$)heteroaryl, ($C_6$–$C_{10}$)aryl($C_6$–$C_{10}$)aryl($C_1$–$C_6$)alkyl or ($C_6$–$C_{10}$) aryl($C_1$–$C_6$)alkoxy($C_1$–$C_6$)alkyl, wherein each of said ($C_6$–$C_{10}$)aryl or ($C_2$–$C_9$)heteroaryl moieties is optionally substituted on any of the ring carbon atoms capable of forming an additional bond by one or more substituents per ring, independently selected from fluoro, chloro, bromo, ($C_1$–$C_6$)alkyl, ($C_1$–$C_6$)alkoxy, perfluoro ($C_1$–$C_3$)alkyl, perfluoro($C_1$–$C_3$)alkoxy and ($C_6$–$C_{10}$) aryloxy;

with the proviso that when X is >C=O and Z is >NR¹, then R¹ must be hydrogen, ($C_1$–$C_6$)alkyl, ($C_6$–$C_{10}$)aryl ($C_1$–$C_6$)alkyl or ($C_2$–$C_9$)heteroaryl ($C_1$–$C_6$)alkyl;

or the pharmaceutically acceptable salts thereof.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl. Preferred heteroaryls include pyridyl, furyl, thienyl, isothiazolyl, pyrazinyl, pyrimidyl, pyrazolyl, isoxazolyl, thiazolyl or oxazolyl. Most preferred heteroaryls include pyridyl, furyl or thienyl.

The term "terminal ring" refers to the ring furthest from the point of attachment of the substituent (i.e. the terminal ring in the group ($C_6$–$C_{10}$)aryl($C_1$–$C_6$)alkyl($C_2$–$C_9$) heteroaryl is aryl).

The compound of formula I may have chiral centers and therefore exist in different enantiomeric forms. This invention relates to all optical isomers, tautomers and stereoisomers of the compounds of formula I and mixtures thereof wherein the bicyclo [3.3.0] ring system is cis fused.

Other compounds of the invention relate to a compound of formula I, wherein X is —CH₂— and Z is —CH₂—.

Other compounds of the invention also relate to a compound of formula I, wherein X is >C=O and Z is —CH₂—.

Preferred compounds of the invention relate to a compound of formula I wherein Z is >NR¹, more preferably wherein R¹ is hydrogen, ($C_1$–$C_6$)alkyl, ($C_6$–$C_{10}$)aryl($C_1$–$C_6$) alkyl or ($C_2$–$C_9$)heteroaryl($C_1$–$C_6$)alkyl.

Other preferred compounds of the invention relate to a compound of formula I wherein X is —CH$_2$— and Z is >NR$^1$, more preferably wherein R$^1$ is hydrogen, (C$_1$–C$_8$)alkyl, (C$_6$–C$_{10}$)aryl(C$_1$–C$_6$)alkyl or (C$_2$–C$_9$)heteroaryl(C$_1$–C$_6$)alkyl.

Other preferred compounds of the invention relate to a compound of formula I wherein X is >C=O and Z is >NR$^1$, more preferably wherein R$^1$ is hydrogen, (C$_1$–C$_8$)alkyl, (C$_6$–C$_{10}$)aryl(C$_1$–C$_6$)alkyl or (C$_2$–C$_9$)heteroaryl(C$_1$–C$_6$)alkyl.

More preferred compounds of the present invention relate to a compound of formula I, wherein Q is optionally substituted (C$_6$–C$_{10}$)aryl, (C$_6$–C$_{10}$)aryloxy(C$_6$–C$_{10}$)aryl, (C$_2$–C$_9$)heteroaryloxy(C$_6$–C$_{10}$)aryl or (C$_6$–C$_{10}$)aryl(C$_1$–C$_6$)alkoxy(C$_6$–C$_{10}$)aryl, preferably substituted with zero to three substituents (most preferably zero, one or two substituents) independently selected from hydrogen, fluoro, chloro, (C$_1$–C$_6$)alkyl or (C$_1$–C$_6$)alkoxy. When the compound of formula I possesses a substituent, that substituent is most preferably in the para or ortho position of the terminal ring.

Specific preferred compounds of formula I are selected from the group consisting of:

[3aR-(3aβ,5α, 6aβ]-5-[4-(4-fluoro-phenoxy)-benzenesulfonylamino]-tetrahydro-cyclopenta[1,3]dioxole-5-carboxylic acid hydroxyamide,
[3aS-(3aα, 5α, 6aα]-5-[4-(4-fluoro-phenoxy)-benzenesulfonylamino]-tetrahydro-cyclopenta[1,3]dioxole-5-carboxylic acid hydroxyamide,
[3aR-(3aβ, 5α, 6aβ]-5-[4-(4-chloro-phenoxy)-benzenesulfonylamino]-tetrahydro-cyclopenta[1,3]dioxole-5-carboxylic acid hydroxyamide,
[3aS-(3aα,5α, 6aα]-5-[4-(4-chloro-phenoxy)-benzenesulfonylamino]-tetrahydro-cyclopenta[1,3]dioxole-5-carboxylic acid hydroxyamide,
[3aR-(3aβ,5α, 6aβ]-5-[4-(4-Fluoro-phenoxy)-benzenesulfonylamino]-2-oxo-tetrahydro-cyclopenta[1,3]dioxole-5-carboxylic acid hydroxyamide,
[3aS-(3aα, 5α, 6aα]-5-(4-Benzyloxy-benzenesulfonylamino)-tetrahydro-cyclopenta[1,3]dioxole-5-carboxylic acid hydroxyamide and
[3aS-(3aα, 5α, 6aα]-5-[4-(4-Fluoro-benzyloxy)-benzenesulfonylamino]-tetrahydro-cyclopenta[1,3]dioxole-5-carboxylic acid hydroxyamide.

Other compounds of formula I are selected from the group consisting of:

5-[4-(4-Chloro-benzyloxy)-benzenesulfonylamino]-tetrahydro-cyclopenta[1,3]dioxole-5-carboxylic acid hydroxyamide,
5-[4-(2-Methyl-benzyloxy)-benzenesulfonylamino]-tetrahydro-cyclopenta[1,3]dioxole-5-carboxylic acid hydroxyamide,
5-[4-(4-Fluoro-2-methyl-benzyloxy)-benzenesulfonylamino]-tetrahydro-cyclopenta[1,3]dioxole-5-carboxylic acid hydroxyamide,
5-[4-(5-Fluoro-2-methyl-benzyloxy)-benzenesulfonylamino]-tetrahydro-cyclopenta[1,3]dioxole-5-carboxylic acid hydroxyamide,
5-[4-(Pyridin-4-yloxy)-benzenesulfonylamino]-tetrahydro-cyclopenta[1,3]dioxole-5-carboxylic acid hydroxyamide,
5-[4-(Pyridin-3-yloxy)-benzenesulfonylamino]-tetrahydro-cyclopenta[1,3]dioxole-5-carboxylic acid hydroxyamide,
5-[4-(Pyridin-2-yloxy)-benzenesulfonylamino]-tetrahydro-cyclopenta[1,3]dioxole-5-carboxylic acid hydroxyamide,
5-[4-(Pyridin4-ylmethoxy)-benzenesulfonylamino]-tetrahydro-cyclopenta[1,3]dioxole-5-carboxylic acid hydroxyamide,
5-[4-(2-Pyridin-4-yl-ethoxy)-benzenesulfonylamino]-tetrahydro-cyclopenta[1,3]dioxole-5-carboxylic acid hydroxyamide,
5-{4-[2-(4-Fluoro-phenyl)-ethoxy]-benzenesulfonylamino}-tetrahydro-cyclopenta[1,3]dioxole-5-carboxylic acid hydroxyamide,
5-[4-(Thiazol4-ylmethoxy)-benzenesulfonylamino]-tetrahydro-cyclopenta[1,3]dioxole-5-carboxylic acid hydroxyamide,
5-[4-(2-Chloro-thiazol4-ylmethoxy)-benzenesulfonylamino]-tetrahydro-cyclopenta[1,3]dioxole-5-carboxylic acid hydroxyamide,
5-(4'-Fluoro-biphenyl-4-sulfonylamino)-tetrahydro-cyclopenta[1,3]dioxole-5-carboxylic acid hydroxyamide,
5-[4-(Benzothiazol-2-yloxy)-benzenesulfonylamino]-tetrahydro-cyclopenta[1,3]dioxole-5-carboxylic acid hydroxyamide,
5-[5-(4-Fluoro-phenoxy)-furan-2-sulfonylamino]-tetrahydro-cyclopenta[1,3]dioxole-5-carboxylic acid hydroxyamide,
5-(5-Pyridin-2-yl-thiophene-2-sulfonylamino)-tetrahydro-cyclopenta[1,3]dioxole-5-carboxylic acid hydroxyamide,
5-[4-(4-Chloro-phenoxy)-benzenesulfonylamino]-2-oxo-tetrahydro-cyclopenta[1,3]dioxole-5-carboxylic acid hydroxyamide,
5-[4-(4-Fluoro-benzyloxy)-benzenesulfonylamino]-2-oxo-tetrahydro-cyclopenta[1,3]dioxole-5-carboxylic acid hydroxyamide,
5-[4-(4-Chloro-benzyloxy)-benzenesulfonylamino]-2-oxo-tetrahydro-cyclopenta[1,3]dioxole-5-carboxylic acid hydroxyamide,
5-[4-(2,5-Difluoro-benzyloxy)-benzenesulfonylamino]-2-oxo-tetrahydro-cyclopenta[1,3]dioxole-5-carboxylic acid hydroxyamide,
5-[4-(2-Methyl-benzyloxy)-benzenesulfonylamino]-2-oxo-tetrahydro-cyclopenta[1,3]dioxole-5-carboxylic acid hydroxyamide,
5-[4-(4-Fluoro-2-methyl-benzyloxy)-benzenesulfonylamino]-2-oxo-tetrahydro-cyclopenta[1,3]dioxole-5-carboxylic acid hydroxyamide,
5-[4-(5-Fluoro-2-methyl-benzyloxy)-benzenesulfonylamino]-2-oxo-tetrahydro-cyclopenta[1,3]dioxole-5-carboxylic acid hydroxyamide,
5-[4-(Pyridin-4-yloxy)-benzenesulfonylamino]-2-oxo-tetrahydro-cyclopenta[1,3]dioxole-5-carboxylic acid hydroxyamide,
5-[4-(Pyridin-3-yloxy)-benzenesulfonylamino]-2-oxo-tetrahydro-cyclopenta[1,3]dioxole-5-carboxylic acid hydroxyamide,
5-[4-(Pyridin-2-yloxy)-benzenesulfonylamino]-2-oxo-tetrahydro-cyclopenta[1,3]dioxole-5-carboxylic acid hydroxyamide,
5-[4-(Pyridin-4-ylmethoxy)-benzenesulfonylamino]-2-oxo-tetrahydro-cyclopenta[1,3]dioxole-5-carboxylic acid hydroxyamide,
5-[4-(2-Pyridin-4-yl-ethoxy)-benzenesulfonylamino]-2-oxo-tetrahydro-cyclopenta[1,3]dioxole-5-carboxylic acid hydroxyamide,
5-{4-[2-(4-Fluoro-phenyl)-ethoxy]-benzenesulfonylamino}-2-oxo-tetrahydro-cyclopenta[1,3]dioxole-5-carboxylic acid hydroxyamide,
5-[4-(Thiazol-4-ylmethoxy)-benzenesulfonylamino]-2-oxo-tetrahydro-cyclopenta[1,3]dioxole-5-carboxylic acid hydroxyamide, 5-[4-(2-Chloro-thiazol-4-ylmethoxy)-benzenesulfonylamino]-2-oxo-tetrahydro-cyclopenta[1,3]dioxole-5-carboxylic acid hydroxyamide, 5-(4'-Fluoro-biphenyl-4-sulfonylamino)-2-oxo-tetrahydro-cyclopenta[1,3]dioxole-5-carboxylic acid hydroxyamide, 5-[4-(Benzothiazol-2-yloxy)-benzenesulfonylamino]-2-oxo-tetrahydro-cyclopenta[1,3]dioxole-5-carboxylic acid hydroxyamide, 5-[5-(4-Fluoro-phenoxy)-furan-2-sulfonylamino]-2-oxo-tetrahydro-cyclopenta[1,3]dioxole-5-carboxylic acid hydroxyamide, 5-(5-Pyridin-2-yl-thiophene-2-sulfonylamino)-2-oxo-tetrahydro-cyclopenta[1,3]dioxole-5-carboxylic acid hydroxyamide, 3-[[4-(4-Fluoro-phenoxy)-benzenesulfonyl]-(5-hydroxycarbamoyl-tetrahydro-cyclopenta[1,3]dioxol-5-yl)-amino]-propionic acid, 3-[[4-(4-Chloro-phenoxy)-benzenesulfonyl]-(5-hydroxycarbamoyl-tetrahydro-cyclopenta[1,3]dioxol-5-yl)-amino]-propionic acid, 3-[[4-(4-Fluoro-benzyloxy)-benzenesulfonyl]-(5-hydroxycarbamoyl-tetrahydro-cyclopenta[1,3]dioxol-5-yl)-amino]-propionic acid, 3-[[4-(4-Chloro-benzyloxy)-benzenesulfonyl]-(5-hydroxycarbamoyl-tetrahydro-cyclopenta[1,3]dioxol-5-yl)-amino]-propionic acid, 3-[[4-(2,5-Difluoro-benzyloxy)-benzenesulfonyl]-(5-hydroxycarbamoyl-tetrahydro-cyclopenta[1,3]dioxol-5-yl)-amino]-propionic acid, 3-[[4-(2-Methyl-benzyloxy)-benzenesulfonyl]-(5-hydroxycarbamoyl-tetrahydro-cyclopenta[1,3]dioxol-5-yl)-amino]-propionic acid, 3-[[4-(4-Fluoro-2-methyl-benzyloxy)-benzenesulfonyl]-(5-hydroxycarbamoyl-tetrahydro-cyclopenta[1,3]dioxol-5-yl)-amino]-propionic acid, 3-[[4-(5-Fluoro-2-methyl-benzyloxy)-benzenesulfonyl]-(5-hydroxycarbamoyl-tetrahydro-cyclopenta[1,3]dioxol-5-yl)-amino]-propionic acid, 5-[[4-(4-Fluoro-phenoxy)-benzenesulfonyl]-(3-methyl-butyl)-amino]-tetrahydro-cyclopenta[1,3]dioxole-5-carboxylic acid hydroxyamide, 5-{[4-(4-Fluoro-phenoxy)-benzenesulfonyl]-thiazol-4-ylmethyl-amino}-tetrahydro-cyclopenta[1,3]dioxole-5-carboxylic acid hydroxyamide, 5-{[4-(4-Fluoro-benzyloxy)-benzenesulfonyl]-thiazol-4-ylmethyl-amino}-tetrahydro-cyclopenta[1,3]dioxole-5-carboxylic acid hydroxyamide, 5-{(4-Fluoro-benzenesulfonyl)-[2-(4-fluoro-phenyl)-ethyl]-amino}-tetrahydro-cyclopenta[1,3]dioxole-5-carboxylic acid hydroxyamide, 5-[[4-(2-Pyridin-4-yl-ethoxy)-benzenesulfonyl]-(3-methyl-butyl)-amino]-tetrahydro-cyclopenta[1,3]dioxole-5-carboxylic acid hydroxyamide, 5-[4-(4-Fluoro-phenoxy)-benzenesulfonylmethyl]-tetrahydro-cyclopenta[1,3]dioxole-5-carboxylic acid hydroxyamide, 5-[4-(4-Chloro-phenoxy)-benzenesulfonylmethyl]-tetrahydro-cyclopenta[1,3]dioxole-5-carboxylic acid hydroxyamide, 5-[4-(4-Fluoro-benzyloxy)-benzenesulfonylmethyl]-tetrahydro-cyclopenta[1,3]dioxole-5-carboxylic acid hydroxyamide, 5-[4-(4-Chloro-benzyloxy)-benzenesulfonylmethyl]-tetrahydro-cyclopenta[1,3]dioxole-5-carboxylic acid hydroxyamide, 5-[4-(2,5-Difluoro-benzyloxy)-benzenesulfonylmethyl]-tetrahydro-cyclopenta[1,3]dioxole-5-carboxylic acid hydroxyamide, 5-[4-(2-Methyl-benzyloxy)-benzenesulfonylmethyl]-tetrahydro-cyclopenta[1,3]dioxole-5-carboxylic acid hydroxyamide, 5-[4-(4-Fluoro-2-methyl-benzyloxy)-benzenesulfonylmethyl]-tetrahydro-cyclopenta[1,3]dioxole-5-carboxylic acid hydroxyamide, 5-[4-(5-Fluoro-2-methyl-benzyloxy)-benzenesulfonylmethyl]-tetrahydro-cyclopenta[1,3]dioxole-5-carboxylic acid hydroxyamide, 5-[4-(Pyridin4-yloxy)-benzenesulfonylmethyl]-tetrahydro-cyclopenta[1,3]dioxole-5-carboxylic acid hydroxyamide, 5-[4-(Pyridin-3-yloxy)-benzenesulfonylmethyl]-tetrahydro-cyclopenta[1,3]dioxole-5-carboxylic acid hydroxyamide, 5-[4-(Pyridin-2-yloxy)-benzenesulfonylmethyl]-tetrahydro-cyclopenta[1,3]dioxole-5-carboxylic acid hydroxyamide, 5-[4-(Pyridin4-ylmethoxy)-benzenesulfonylmethyl]-tetrahydro-cyclopenta[1,3]dioxole-5-carboxylic acid hydroxyamide, 5-[4-(2-Pyridin-4-yl-ethoxy)-benzenesulfonylmethyl]-tetrahydro-cyclopenta[1,3]dioxole-5-carboxylic acid hydroxyamide, 5-{4-[2-(4-Fluoro-phenyl)-ethoxy]-benzenesulfonylmethyl}-tetrahydro-cyclopenta[1,3]dioxole-5-carboxylic acid hydroxyamide, 5-[4-(Thiazol-4-ylmethoxy)-benzenesulfonylmethyl]-tetrahydro-cyclopenta[1,3]dioxole-5-carboxylic acid hydroxyamide, 5-[4-(2-Chloro-thiazol-4-ylmethoxy)-benzenesulfonylmethyl]-tetrahydro-cyclopenta[1,3]dioxole-5-carboxylic acid hydroxyamide, 5-(4'-Fluoro-biphenyl-4-sulfonylmethyl)-tetrahydro-cyclopenta[1,3]dioxole-5-carboxylic acid hydroxyamide, 5-[4-(Benzothiazol-2-yloxy)-benzenesulfonylmethyl]-tetrahydro-cyclopenta[1,3]dioxole-5-carboxylic acid hydroxyamide, 5-[5-(4-Fluoro-phenoxy)-furan-2-sulfonylmethyl]-tetrahydro-cyclopenta[1,3]dioxole-5-carboxylic acid hydroxyamide, 5-(5-Pyridin-2-yl-thiophene-2-sulfonylmethyl)-tetrahydro-cyclopenta[1,3]dioxole-5-carboxylic acid hydroxyamide, 5-[4-(4-Fluoro-phenoxy)-benzenesulfonylmethyl]-2-oxo-tetrahydro-cyclopenta[1,3]dioxole-5-carboxylic acid hydroxyamide, 5-[4-(4-Chloro-phenoxy)-benzenesulfonylmethyl]-2-oxo-tetrahydro-cyclopenta[1,3]dioxole-5-carboxylic acid hydroxyamide, 5-[4-(4-Fluoro-benzyloxy)-benzenesulfonylmethyl]-2-oxo-tetrahydro-cyclopenta[1,3]dioxole-5-carboxylic acid hydroxyamide, 5-[4-(4-Chloro-benzyloxy)-benzenesulfonylmethyl]-2-oxo-tetrahydro-cyclopenta[1,3]dioxole-5-carboxylic acid hydroxyamide, 5-[4-(2,5-Difluoro-benzyloxy)-benzenesulfonylmethyl]-2-oxo-tetrahydro-cyclopenta[1,3]dioxole-5-carboxylic acid hydroxyamide, 5-[4-(2-Methyl-benzyloxy)-benzenesulfonylmethyl]-2-oxo-tetrahydro-cyclopenta[1,3]dioxole-5-carboxylic acid hydroxyamide, 5-[4-(4-Fluoro-2-methyl-benzyloxy)-benzenesulfonylmethyl]-2-oxo-tetrahydro-cyclopenta[1,3]dioxole-5-carboxylic acid hydroxyamide, 5-[4-(5-Fluoro-2-methyl-benzyloxy)-benzenesulfonylmethyl]-2-oxo-tetrahydro-cyclopenta[1,3]dioxole-5-carboxylic acid hydroxyamide, 5-[4-(Pyridin-4-yloxy)-benzenesulfonylmethyl]-2-oxo-tetrahydro-cyclopenta[1,3]dioxole-5-carboxylic acid hydroxyamide, 5-[4-(Pyridin-3-yloxy)-benzenesulfonylmethyl]-2-oxo-tetrahydro-cyclopenta[1,3]dioxole-5-carboxylic acid hydroxyamide, 5-[4-(Pyridin-2-yloxy)-benzenesulfonylmethyl]-2-oxo-tetrahydro-cyclopenta[1,3]dioxole-5-carboxylic acid hydroxyamide, 5-[4-(Pyridin-4-ylmethoxy)-benzenesulfonylmethyl]-2-oxo-tetrahydro-cyclopenta[1,3]dioxole-5-carboxylic acid hydroxyamide, 5-[4-(2-Pyridin-4-yl-ethoxy)-benzenesulfonylmethyl]-2-oxo-tetrahydro-cyclopenta[1,3]dioxole-5-carboxylic acid hydroxyamide, 5-{4-[2-(4-Fluoro-phenyl)-ethoxy]-benzenesulfonylmethyl}-2-oxo-tetrahydro-cyclopenta[3]dioxole-5-carboxylic acid hydroxyamide, 5-[4-(Thiazol-4-ylmethoxy)-benzenesulfonylmethyl]-2-oxo-tetrahydro-cyclopenta[1,3]dioxole-5-carboxylic acid hydroxyamide, 5-[4-(2-Chloro-thiazol-4-ylmethoxy)-benzenesulfonylmethyl]-2-oxo-tetrahydro-cyclopenta[1,3]dioxole-5-carboxylic acid hydroxyamide, 5-(4'-Fluoro-biphenyl-4-sulfonylmethyl)-2-oxo-tetrahydro-cyclopenta[1,3]dioxole-5-carboxylic acid hydroxyamide, 5-[4-(Benzothiazol-2-yloxy)-benzenesulfonylmethyl]-2-oxo-tetrahydro-cyclopenta[1,3]dioxole-5-carboxylic acid hydroxyamide, 2-Benzyl-5-[4-(2,4-difluorobenzyloxy)-benzenesulfonylamino]tetrahydrocyclopenta[1,3]dioxole-5-carboxylic acid hydroxyamide, 2-(2-Methoxyethyl)-5-[4-(quinolin-5-ylmethoxy)-benzenesulfonylamino]-tetrahydrocyclopenta[1,3]dioxole-5-carboxylic acid hydroxyamide, 5-[4-(4-Fluorophenoxy)-benzenesulfonylamino]-2-(2-methoxyethyl)-tetrahydrocyclopenta[1,3]dioxole-5-carboxylic acid hydroxyamide, 5-[4-(5-Chloropyridin-2-yloxy)-benzenesulfonylamino]-2-furan-2-ylmethyl-2-methyl-tetrahydrocyclopenta[1,3]dioxole-5-carboxylic acid hydroxyamide, 5-[4-(4-Chlorophenoxy)-benzenesulfonylmethyl]-2-ethoxymethyltetrahydrocyclopenta-[1,3]dioxole-5-carboxylic acid hydroxyamide, 3-[(5-Hydroxycarbamoyl-2-phenethyltetrahydrocyclopenta[1,3]dioxol-5-yl)-(4-phenoxybenzenesulfonyl)-amino]-propionic acid, 5-[5-(4-Fluoro-phenoxy)-furan-2-sulfonylmethyl]-2-oxo-tetrahydro-cyclopenta[1,3]dioxole-5-carboxylic acid hydroxyamide, and 5-(5-Pyridin-2-yl-thiophene-2-sulfonylmethyl)-2-oxo-tetrahydro-cyclopenta[1,3]dioxole-5-carboxylic acid hydroxyamide.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of formula I or a pharmaceutically acceptable salt thereof effective in treating such a condition.

The present invention also relates to the treatment of diseases characterized by matrix metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably ADAM-17) in a mammal, including a human, comprising administering to said mammal an effective amount of a compound of formula I or a pharmaceutically acceptable salt thereof.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, mirapex, MAOB inhibitors such as segeline and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene or fosomax and immunosuppressant agents such as FK-506 and rapamycin.

DETAILED DESCRIPTION OF THE INVENTION

The following reaction Scheme illustrates the preparation of the compounds of the present invention. Unless otherwise indicated, n, X, Z, Q and $R^1$, $R^2$, $R^3$, and $R^4$ in the reaction Schemes and the discussion that follows is defined as above.

SCHEME 1

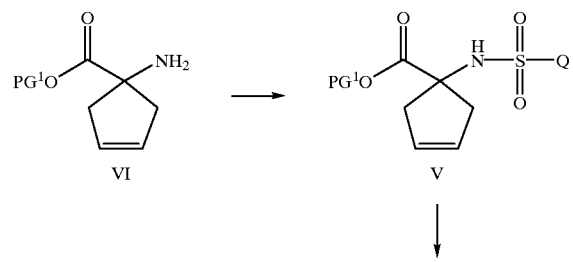

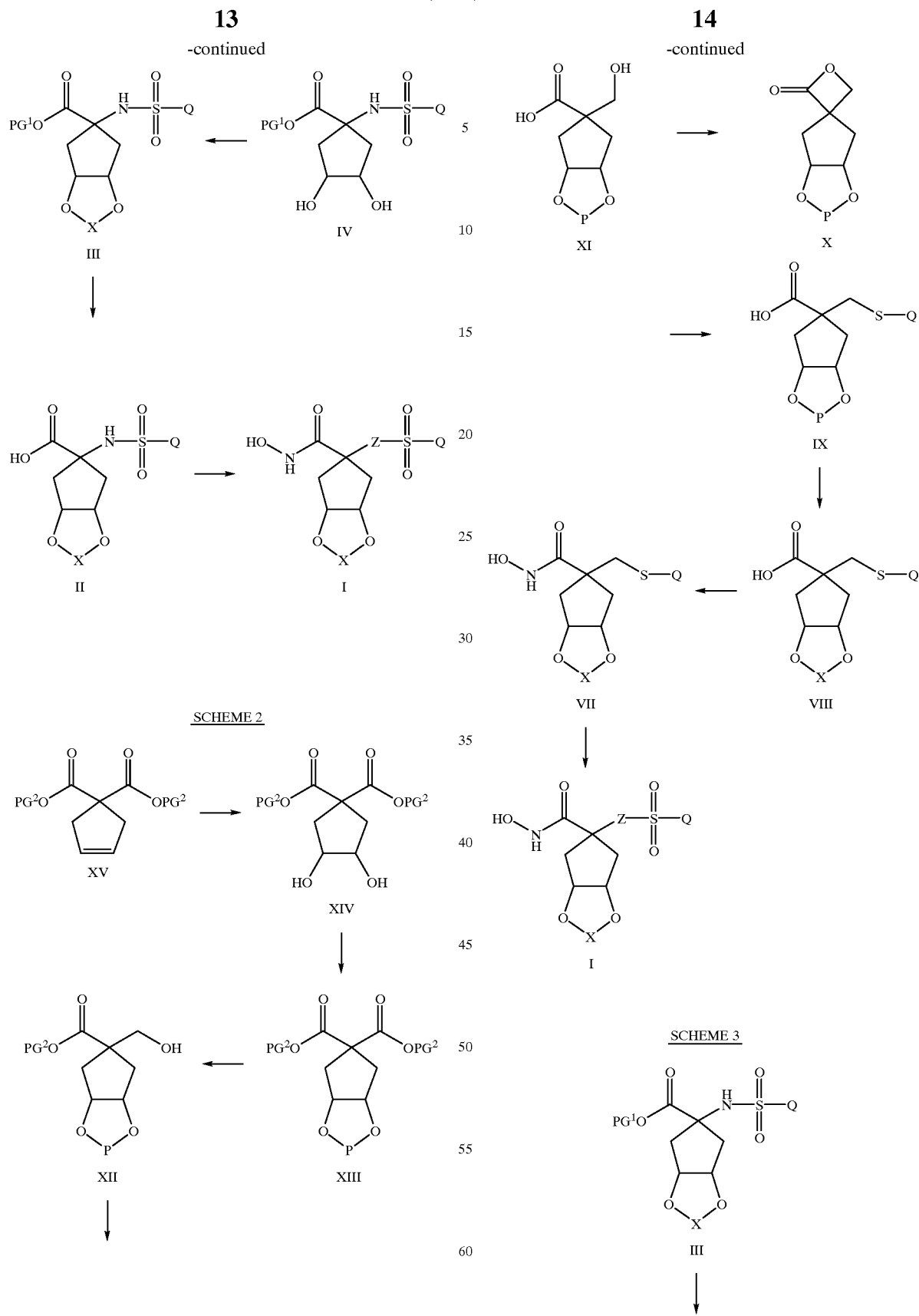

15
-continued

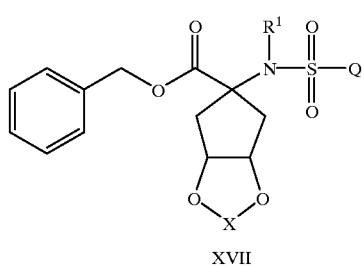

XVII

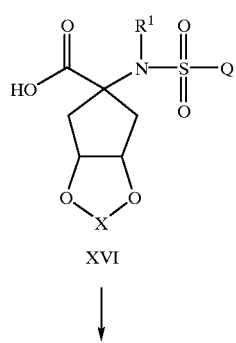

XVI

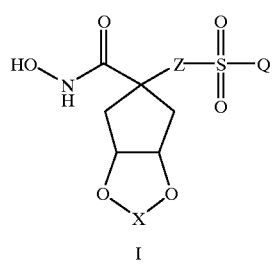

I

SCHEME 4

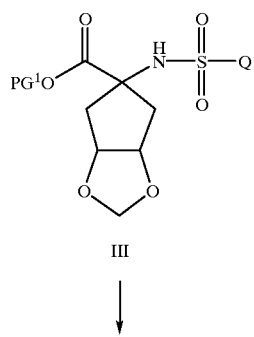

III

16
-continued

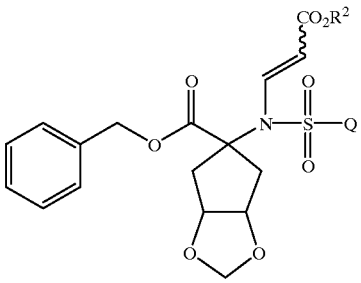

XIX

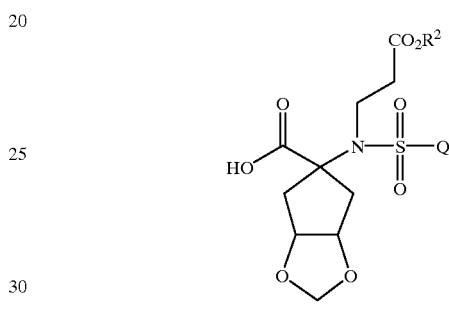

XVIII

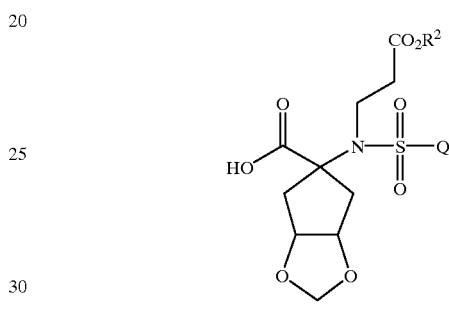

I

Scheme 1 refers to the preparation of compounds of the formula I, wherein Z is >$NR^1$, and $R^1$ is hydrogen. Referring to Scheme 1, compounds of formula I are prepared from compounds of formula II by activation of the carboxylic acid moiety in compounds of formula II followed by treatment of the activated acid with hydroxylamine or a protected hydroxylamine equivalent that is then deprotected to form the hydroxamic acid. Activation of the carboxyl group of formula II is achieved through the action of a suitable activating agent such as dialkyl carbodiimides, benzotriazol-1-yloxyl)tris(dialkylamino)-phosphonium salts, or oxalyl chloride in the presence of a catalytic amount of N,N-dimethylformamide (benzotriazol-1-yloxy-tris(dimethylamino)phosphonium hexafluorophosphate is preferred). Generally, the hydroxylamine or protected hydroxylamine equivalent is generated in situ from a salt form, such as hydroxylamine hydrochloride, in the presence of an amine base such as triethylamine, or N,N-diisopropylethylamine. Suitable protected hydroxylamines include O-tert-butylhydroxylamine, O-allylhydroxylamine, O-tert-butyldimethylsilylhydroxylamine, O-trimethylsilylethylhydroxylamine, O-benzylhydroxylamine, or N,O-bistrimethylsilylhydroxylamine. Removal of the protecting group is carried out by hydrogenolysis in the instance where O-benzylhydroxylamine is used (5% palladium on barium sulfate is the preferred catalyst) or by treatment with a strong acid such as trifluoroacetic acid in the situation where O-tert-butylhydroxylamine or O-trimethylsilylethylhydroxylamine is used. When O-allylhydroxylamine is employed, the allyl group is preferably removed by treatment with ammonium formate in the presence of a catalytic amount of tetrakis (triphenylphosphine)palladium(0) in aqueous acetonitrile at 60° C. or by treatment with piperidine in the presence of a catalytic amount of allylpalladium chloride dimer and diphenylphosphinoethane in tetrahydrofuran (THF) at about 0° C. to about 35° C., preferably about 23° C. In the case where N,O-bis-trimethylsilylhydroxylamine is used (preferably generated in situ from trimethylsilylchloride and hydroxylamine hydrochloride in pyridine at about 0° C.), the silyl protective groups are removed by treatment with dilute aqueous acid such as 1 N hydrochloric acid. Suitable solvents for the aforesaid activation and hydroxylamine reaction include dichloromethane, N,N-dimethylformamide, or tetrahydrofuran, preferably dichloromethane. The aforesaid activation and hydroxylamine reactions are run at temperatures between about 0° C. to about 60° C. (23° C. is preferred) for periods of time between about 1 hour and about 20 hours (4 hours is preferred).

Compounds of formula II are prepared from compounds of formula III by removal of the protective group $PG^1$ to form a carboxylic acid. In cases where the protecting group $PG^1$ is methyl or ethyl, this conversion is achieved by saponification with a suitable source of hydroxide such as sodium or lithium hydroxide (lithium hydroxide is preferred). Preferably the saponification is conducted with stirring, in an aqueous solvent mixture such as tetrahydrofuran-methanol-water or 1,4-dioxane-methanol-water at a temperature between about 0° C. to near the boiling point of the solvent system (about 60° C. is preferred). In cases where the protecting group $PG^1$ is benzyl, the conversion is achieved by hydrogenolysis of the benzyl group. The hydrogenolysis is carried out in a suitable solvent such as ethanol, methanol, or ethyl acetate under an atmosphere of hydrogen, in the presence of a catalyst such a 10% palladium on carbon. Generally, reactions involving the removal of protecting group $PG^1$ are run for periods of time between about 30 minutes to about 8 hours, preferably about 4 hours. Unless otherwise mentioned, the aforesaid reactions are performed at a temperature from about 0° C. to about 25° C., preferably about 23° C.

Alternatively compounds of formula III can be converted directly to compounds of formula I through the action of hydroxylamine. Preferably, the protecting group $PG^1$ is methyl. Suitable solvents include methanol, ethanol, or 2-propanol, preferably methanol. For this reaction the preferred method for generating the hydroxylamine is by treatment of hydroxylamine hydrochloride with potassium hydroxide. The reaction is performed at a temperature between about 0° C. to about 23° C. (0° C. is preferred) for a period of time from about 10 minutes to about 4 hours (2 hours is preferred).

Compounds of formula III are prepared from compounds of formula IV by the reaction of the cis diol moiety in compounds of formula IV with a source of active methylene, active carbonyl or a compound of the formula $R^3R^4C=O$. Sources of active methylene include formaldehyde, dimethoxymethane, and dibromomethane. Active carbonyl sources include phosgene, 1,1'-carbonyldiimidazole, and triphosgene (bis(trichloromethyl)carbonate). The preferred method of preparing compounds of formula III, wherein X is $CH_2$, is by reaction of compounds of formula IV with dimethoxymethane in the presence of a strong acid such as p-toluenesulfonic acid, camphorsulfonic acid, or Amberlsyt® 15 (Amberlyst® 15 is preferred). Preferably this methylenation reaction is conducted in a solvent such as benzene or dichloromethane (dichloromethane is preferred) at a temperature between about 23° C. to the boiling point of the solvent mixture (preferably 40° C.) for a period of around 2 hours to about 24 hours, preferably about 17 hours. Preferably the aforesaid reaction is conducted with the use of a Dean-Stark trap charged with 4 angstrom sieves (Å). The preferred method of preparing compounds of formula III, wherein X is CO, is by reaction of compounds of formula IV with 1,1-carbonyldiimidazole. Preferably this carbonylation reaction is performed in a solvent such as toluene, dichloromethane, or tetrahydrofuran (dichloromethane is preferred), at a temperature between about 0° C. to about 35° C. (about 23° C. is preferred) for a period of time from about 1 hour to about 2 days hours (1 day is preferred). The preferred methods for preparing compounds of the formula III, wherein X is $>CR^3R^4$ and wherein one of $R^3$ or $R^4$ is other than hydrogen, is by reaction of compounds of the formula IV with an aldehyde or ketone compound of the formula $R^3R^4C=O$ in the presence of an acid, such as p-toluene sulfonic acid, under dehydrating conditions such as refluxing the reaction mixture in a high boiling solvent such as toluene or benzene in the presence of a Dean-Stark trap or 4 Å molecular sieves. Aldehydes or ketones of the formula $R^3R^4C=O$ are commercially available or can be made by methods well known to those of ordinary skill in the art.

Compounds of the formula IV are prepared from compounds of the formula V by bis-hydroxylation. Preferably the bis-hydroxylation reaction is performed using osmium tetroxide in a suitable solvent or solvent mixture such as pyridine, acetone-water, or tetrahydrofuran-water. The use of a catalytic amount of osmium tetroxide and a stoichiometric amount of a co-oxidant such as 4-methylmorpholine N-oxide or trimethyl amine N-oxide in a mixture of tetrahydrofuran-water is preferred. The aforesaid reaction is run at a temperature between about 0° C. to about 35° C., preferably at about 23° C. for a time period of about 1 hour to about 8 hours (2 hours is preferred). Compounds of formula IV produced in this way are obtained as mixture of diastereomers, which can be separated by crystallization, chromatographic means, or by chemical methods. Chemical methods include subjecting the mixture of diastereomers to lactonization conditions, followed by chromatographic separation of the resulting lactone and the remaining diol isomer. The preferred method of lactonization involves heating of the mixture of diastereomers of formula IV in toluene at reflux in the presence of p-toluenesulfonic acid or Amberlyst® 15 for a period of about 20 hours, using a Dean-Stark trap charged with 4 angstrom sieves.

Compounds of formula V, wherein $PG^1$ is methyl, ethyl, or benzyl, are prepared from compounds of formula VI by reaction with compounds of the formula QSO$_2$Cl. Preferably the aforesaid reaction is run in a suitable solvent such as dichloromethane, tetrahydrofuran, N,N-dimethylformamide. Suitable bases include triethylamine, N,N-diisopropylethylamine. The use of dichloromethane as solvent and N,N-diisopropylethylamine as the base in the presence of a catalytic amount of 4-(dimethylamino) pyridine are preferred. The reaction is stirred at a temperature between about 0° C. to about 35° C., preferably at about 23° C., for a time period between about 2 hours to about 1 day, preferably about 12 hours. Compounds of formula VI wherein PG$^1$ is methyl, ethyl or benzyl are known in the literature (Park, K.-H.; Olmstead, M. M.; Kurth, M. J. J. Org. Chem. 1998, 63, 113–117 see also Kotha, S.; Sreenivasachary, N. Bioorg. Med. Chem. Lett. 1998, 8, 257–260) or can be prepared in an analogous way. Compounds of the formula QSO$_2$Cl are known, and can be prepared according to methods described in PCT publication WO 98/07697, published Feb. 26, 1998, or and PCT publication WO 98/33768 published Aug. 6, 1998, are commercially available, or can be made by methods well known to those of ordinary skill in the art.

Scheme 2 refers to the preparation of compounds of formula I, wherein Z is >CH$_2$. Referring to Scheme 2, a compound of the formula I is prepared from a compound of the formula VII by oxidation of the sulfur. Suitable oxidants include meta-chloroperbenzoic acid, hydrogen peroxide, sodium perborate, or Oxone® (Oxone® is preferred). Preferably the reaction is conducted in a suitable solvent or solvent mixture such as methanol-water, dioxane-water, tetrahydrofuran-water, methylene chloride, or chloroform, preferably methanol-water. Suitable temperatures for the aforesaid reaction range from about 0° C. to about 60° C., preferably the temperature may range from about 20° C. to about 25° C. (i.e. room temperature). The reaction is complete within about 0.5 hours to about 24 hours, preferably about 16 hours.

Compounds of the formula VII are prepared from compounds of the formulas VIII as described in Scheme 1 for the preparation of compounds of formula I.

Compounds of formula VIII, wherein X is >CO, can be prepared from compounds of formula IX by removal of the protective group P, followed by cyclic carbonate formation. Removal of the preferred protective group, P equal to >CMe$_2$, is achieved by a hydrolysis reaction. Preferably this hydrolysis is conducted with aqueous hydrochloric acid in a mixture of tetrahydrofuran and water at a temperature of about 23° C. Formation of the cyclic carbonate is conducted as described in preparation 1. Compounds of the formula VIII wherein X is >CR$^3$R$^4$ can be prepared from compounds of the formula IX by methods analogous to the methods of Scheme 1 for the conversion of compounds of formula IV to formula III. Compounds of formula IX, wherein P is CH$_2$, are compounds of formula VIII, wherein X is CH$_2$, and thus can be converted directly to compounds of formula VII as described above.

Compounds of the formula IX can be prepared from compounds of the formula X by reaction with a compound of the formula QSH, wherein Q is as defined above, in the presence of a strong base in an aprotic polar solvent. Suitable bases include sodium hydride, lithium diisopropylamide, potassium t-butoxide, sodium amide or potassium hydride, preferably sodium hydride. Suitable solvents include ethers (such as THF, diethyl ether or 1,2-dimethoxyethane), or N,N-dimethylformamide, preferably the solvent is THF. The aforesaid reaction is conducted at about −78° C. to about 0° C., preferably at about 22° C. for a period of 30 minutes to about 24 hours, preferably about 2 hours.

Compounds of the formula X are prepared from compounds of the formula XI by dehydration in the presence of a tertiary amine base, preferably triethylamine, optionally in the presence of 4-(dimethylamino)pyridine, and a dehydrating agent in an inert solvent. Suitable dehydrating agents include trifluoromethanesulfonic anhydride, methanesulfonic anhydride, methanesulfonyl chloride, p-toluenesulfonyl chloride or benzenesulfonyl chloride, preferably benzenesulfonyl chloride. Suitable solvents include diethyl ether or dichloromethane. The reaction is performed at a temperature from about −80° C. to about 0° C., preferably about 0° C. The reaction is carried out for about 10 minutes to 4 hours, preferably 1 about hour.

The compounds of the formula XI are prepared from a compound of formula XII, wherein PG$^2$ is methyl or ethyl, by saponification with a base, such as lithium hydroxide, in a solvent mixture. Suitable solvent mixtures include water and methanol or water, methanol and THF. The reaction is performed at a temperature from about 60° C. to about 120° C., preferably at about the reflux temperature of the solvent mixture used. The reaction is carried out for about 30 minutes to 24 hours, preferably about 16 hours.

Compounds of formula XII are prepared from compounds of formula XIII by a reduction reaction. In general, a solution of a compound of formula XIII is dissolved in an inert aromatic solvent, preferably benzene or toluene, and cooled at about −40° C. to −20° C., preferably about −40° C. To the cold solution is added a suitable hindered reducing agent, preferably diisobutylaluminum hydride, in an inert aromatic solvent, maintaining the temperature below −25° C. After the addition is complete, the reaction is maintained below 0° C. for about 3 hours. At about −15° C., a protic solvent, preferably ethanol, is added. After stirring at about −15° for about 1 hour, sodium borohydride is added and the reaction is allowed to warm to about room temperature while stirring for a period of 2 to 24 hours, preferably about 16 hours. Compounds of formula XII produced in this way are obtained as a mixture of diastereomers and can be separated by crystallization, chromatography, or chemical methods.

Compounds of formula XIII, wherein P is a diol protective group, are prepared from compounds of formula XIV by reaction with a suitable protective group agent. Suitable protective group agents include dimethoxymethane, dimethoxypropane, benzaldehyde and 2-methoxypropene. The preferred method of preparing compounds of formula XIII, wherein P is CH$_2$, is by reaction of compounds of formula XIV with dimethoxymethane in the presence of a strong acid such as p-toluenesulfonic acid, camphorsulfonic acid, or Amberlsyt® 15 (Amberlyst® 15 is preferred). Preferably this methylenation reaction is conducted in a solvent such as benzene or dichloromethane (dichloromethane is preferred) at a temperature between 23° C. to the boiling point of the solvent mixture (preferably 40° C.) for a period of around 2 hours to about 24 hours, preferably about 17 hours. Preferably the aforesaid reaction is conducted with the use of a Dean-Stark trap charged with 4 angstrom sieves. The preferred protective group P, when P is not CH$_2$, is the acetonide or isopropylidene ketal (P is >CMe$_2$ in formula XIII). The preferred method of preparing compounds of formula XIII, wherein P is >CMe$_2$, is by reaction of compounds of formula XIV with 2-methoxypropene and p-toluenesulfonic acid. Preferably the aforesaid reaction is conducted in a solvent such as benzene, toluene, or dichloromethane (dichloromethane is preferred), for a period of time from about 30 minutes to about 24 hours at a temperature from about 0° C. to about 35° C. (about 23° C. is preferred).

The compounds formula XIV, wherein $PG^2$ is ethyl or methyl, are prepared from compounds of the formula XV, by a bis-hydroxylation reaction. Preferably the bis-hydroxylation reaction is performed using osmium tetroxide in a suitable solvent or solvent mixture such as pyridine, acetone-water, or tetrahydrofuran-water. The use of a catalytic amount of osmium tetroxide and a stoichiometric amount of a co-oxidant such as 4-methyl morpholine N-oxide or trimethyl amine N-oxide in a mixture of tetrahydrofuran-water is preferred. The aforesaid reaction is run at a temperature between about 0° C. to 23° C., preferably at 23° C. for a time period of about 1 hour to about 8 hours (2 hours is preferred).

Compounds of formula XV are commercially available (Frinton Labs, P.O. Box 2428, Vineland, N.J., 08360), or are known in the literature (Depres, J.-P.; Greene, A. E. J. Org. Chem. 1984, 49, 928–931; Chang, S.; Jones II, L.; Chunming, W., Lawrence, H. M.; Grubbs, R. H. Organometallics 1998, 3460–3465; Nugent, W. A.; Feldman, J.; Calabrese, J. C. J. Am. Chem. Soc. 1995, 117, 8992–8998).

Compounds of the formula QSH can be prepared by reaction of an alkyl or aryl halide with sodium sulfhydride as described in Jerry March, *Advanced Organic Chemistry*, 360 and 589 (3rd ed., 1985). Alternatively, compounds of the formula QSH can also be prepared by reaction of an aryl diazonium salt with sodium sulfhydride as described in March id. at 601. Alternatively, compounds of the formula QSH can also be prepared by reaction of a Grignard reagent with sulfur as described in March id. at 550. Alternatively, compounds of the formula QSH can also be prepared by reduction of a sulfonyl chloride, sulfonic acid or disulfide as described in March id. at 1107 and 1110.

Scheme 3 refers to the preparation of compounds of the formula I, wherein Z is $NR^1$ and $R^1$ is $(C_1-C_6)$alkyl, $(C_6-C_{10})$aryl$(C_1-C_6)$alkyl, $(C_2-C_9)$heteroaryl$(C_1-C_6)$alkyl or a group of the formula —$(CH_2)_nCO_2R^2$, wherein n is 1, 3, 4, 5, or 6 and $R^2$ is $(C_1-C_6)$alkyl.

Referring to Scheme 3, compounds of the formula I, wherein X is $CH_2$ and Z is $NR^1$ and $R^1$ is $(C_1-C_6)$alkyl, $(C_6-C_{10})$aryl$(C_1-C_6)$alkyl, $(C_2-C_9)$heteroaryl$(C_1-C_6)$alkyl or a group of the formula —$(CH_2)_nCO_2R^2$, wherein n is 1, 3, 4, 5, or 6 and $R^2$ is $(C_1-C_6)$alkyl, are prepared from compounds of the formula XVI as described in Scheme 1 for the preparation of compounds of formula I from compounds of the formula II.

The compound of formula XVI is prepared from a compound of the formula XVII by removal of the benzyl protecting group. Specifically, the benzyl protecting group is removed by hydrogenolysis using palladium or palladium on carbon in a solvent such as methanol or ethanol, for a period from about 30 minutes to about 48 hours, preferably 16 hours, at a temperature of about 20° C. to about 25° C. (i.e., room temperature).

The compound of formula XVII is prepared from a compound of the formula III, wherein $PG^1$ is benzyl, by reaction with a reactive derivative of an alcohol of the formula $R^1OH$ such as the methanesulfonate, tosylate, chloro, bromo or iodo derivative, preferably the iodo derivative, in the presence of a base such as potassium carbonate or sodium hydride, preferably sodium hydride, and a polar solvent, such as N,N-dimethylformamide. The reaction mixture is stirred at room temperature for a time period between about 60 minutes to about 48 hours, preferably about 16 hours.

The compounds of formula III, wherein $PG^1$ is benzyl, are prepared according to the methods of Scheme 1.

Scheme 4 refers to the preparation of compounds of formula I, wherein X=$CH_2$, Z is >$NR^1$, $R^1$ is a group of the formula —$(CH_2)_2CO_2R^2$ (i.e. n is 2) and $R^2$ is $(C_1-C_6)$alkyl.

Referring to Scheme 4, compounds of said formula I are prepared from compounds of the formula XVIII, wherein $R^2$ is $(C_1-C_6)$alkyl, by reaction with oxalyl chloride or thionyl chloride, preferably oxalyl chloride, and a catalyst, preferably about 2% of N,N-dimethylformamide, in an inert solvent, such as methylene chloride, to form an in situ acid chloride that is subsequently reacted with O-trimethylsilylhydroxylamine in the presence of a base, such as pyridine, 4-N,N-dimethylaminopyridine or triethylamine, preferably pyridine. The reaction is performed at a temperature of about 22° C. (i.e., room temperature) for about 1 to about 12 hours, preferably about 1 hour.

Compounds of the formula XVIII, wherein $R^2$ is $(C_1-C_6)$alkyl, can be prepared from compounds of the formula XIX, wherein $R^2$ is $(C_1-C_6)$alkyl, by reduction in a polar solvent. Suitable reducing agents include hydrogen over palladium and hydrogen over palladium on carbon, preferably hydrogen over palladium on carbon. Suitable solvents include methanol, ethanol and isopropanol, preferably ethanol. The aforesaid reaction is performed at a temperature of about 22° C. (i.e., room temperature) for a period of about 1 to about 7 days, preferably about 2 days.

Compounds of the formula XIX, wherein $R^2$ is $(C_1-C_6)$alkyl, can be prepared from compounds of the formula III, wherein $PG^1$ is benzyl, by Michael addition to a propiolate ester in the presence of a base in a polar solvent. Suitable propiolates are of the formula H—C≡C—$CO_2R^2$, wherein $R^2$ is $(C_1-C_6)$alkyl. Suitable bases include tetrabutylammonium fluoride, potassium carbonate, and cesium carbonate, preferably tetrabutylammonium fluoride. Suitable solvents include tetrahydrofuran, acetonitrile, tert-butanol and N,N-dimethylformamide, preferably tetrahydrofuran. The aforesaid reaction is performed at a temperature of about −10° C. to about 60° C., preferably ranging between 0° C. and about 22° C. (i.e., room temperature). The compounds of formula XIX are obtained as mixtures of geometric isomers about the olefinic double bond; separation of the isomers is not necessary.

Compounds of the formula III, wherein $PG^1$ is benzyl, can be prepared according to the methods of Scheme 1.

Compounds of said formula I, wherein X is $CH_2$, Z is >$NR^1$, $R^1$ is a group of the formula —$(CH_2)_nCO_2R^2$, n is 1 to 6 and $R^2$ is hydrogen are prepared from compounds of formula I, wherein Z is >$NR^1$, $R^1$ is a group of the formula —$(CH_2)_nCO_2R^2$, n is 1 to 6 and $R^2$ is $(C_1-C_6)$alkyl, by saponification using a base such as sodium hydroxide in a protic solvent such as ethanol, methanol or water or a mixture such as water and ethanol, water and toluene, or water and THF. The preferred solvent system is water and ethanol. The reaction is conducted for a period of 30 minutes to 24 hours, preferably about 2 hours.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

Biological Assay

Inhibition of Human Collagenase (MMP-1)

Human recombinant collagenase is activated with trypsin. The amount of trypsin is optimized for each lot of collagenase-1 but a typical reaction uses the following ratio: 5 µg trypsin per 100 µg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 µM→12 µM→1.2 µM→0.12 µM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 ml is then added to appropriate wells of the microfluor plate. Final concentration of collagenase in the assay is 60 ng/ml.

Substrate (DNP-Pro-Cha-Gly-Cys(Me)-His-Ala-Lys (NMA)-$NH_2$) is made as a 5 mM stock in dimethylsulfoxide and then diluted to 20 µM in assay buffer. The assay is initiated by the addition of 50 ml substrate per well of the microfluor plate to give a final concentration of 10 mM.

Fluorescence readings (360 nM excitation, 460 nm emission) are taken at time 0 and then at 20 minute intervals. The assay is conducted at room temperature with a typical assay time of 3 hours.

Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 mM then the inhibitors are assayed at concentrations of 0.3 mM, 0.03 mM, and 0.003 mM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 µM $ZnCl_2$ and 0.02% BRIJ-35 (vol./vol.)) using the following scheme:

10 mM→120 µM→12 µM→1.2 µM→0.12 µM

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 100 ng/mL in assay buffer, 25 µL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-$NH_2$) is diluted in assay buffer to 20 µM. The assay is initiated by addition of 50 µL of diluted substrate yielding a final assay concentration of 10 µM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM $CaCl_2$ and 0.05% BRIJ-35 (vol./vol.)) using the following scheme:

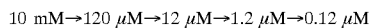

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 200 ng/mL in assay buffer, 25 µL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 µM. The assay is initiated by addition of 50 µL of diluted substrate yielding a final assay concentration of 3 µM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 2.0 hours, at 37° C. and is diluted to 240 ng/ml in assay buffer (50 mM Tris, pH 7.5, 200 mM sodium chloride, 5 mM calcium chloride, 20 mM zinc chloride, 0.02% brij 35). Twenty-five microliters of diluted enzyme is added per well of a 96 well microfluor plate. The enzyme is then diluted in a 1:4 ratio in the assay by the addition of inhibitor and substrate to give a final concentration in the assay of 60 ng/ml.

Stock solutions (10 mM) of inhibitors are made up in dimethylsulfoxide and then diluted in assay buffer as per the inhibitor dilution scheme for inhibition of human collagenase-1 (MMP-1): Twenty-five microliters of each concentration is added in triplicate to the microfluor plate.

The final concentrations in the assay are 30 mM, 3 mmM, 0.3 mmM, and 0.03 mmM.

Substrate (Dnp-Pro-Cha-Gly-Cys(Me)-His-Ala-Lys(NMA)-$NH_2$) is prepared as for inhibition of human collagenase (MMP-1) and 50 µl is added to each well to give a final assay concentration of 10 µM. Fluorescence readings (360 nM excitation; 450 nM emission) are taken at time 0 and every 5 minutes for 1 hour.

Positive controls and negative controls are set up in triplicate as outlined in the MMP-1 assay.

$IC_{50}$'s are determined as per inhibition of human collagenase (MMP-1). If $IC_{50}$'s are reported to be less than 0.03 mM, inhibitors are then assayed at final concentrations of 0.3 mM, 0.03 mmM, 0.003 mmM and 0.0003 mM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 µl of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFa using the R&D ELISA Kit.

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Human Monocyte Assay

Human mononuclear cells are isolated from anti-coagulated human blood using a one-step Ficoll-hypaque separation technique. (2) The mononuclear cells are washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 µCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1%PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. |
| | Make a 100 uM stock of each compound in DMEM in 96 well plate. |
| | Store in freezer overnight. |
| | The next day perform serial dilutions in DMEM with IL-1 to 5 uM, 500 nM, and 50 nM. |
| | Aspirate final wash from wells and add 50 ul of compound from above dilutions to 450 ul of IL-1 media in appropriate wells of the 48 well plates. |
| | Final compound concentrations equal 500 nM, 50 nM, and 5 nM. |
| | All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

All of the compounds that were tested had $IC_{50}$ of less than 30 nM in at least one of the above assays. Preferred compounds of the invention had $IC_{50}$ of less than 10 nM in at least one of the above assays.

For administration to mammals, including humans, for the inhibition of matrix metalloproteinases or mammalian reprolysin, a variety of conventional routes may be used including oral, parenteral (eg., intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

[3aR-(3aβ,5α,6aβ]-5-[4-(4-Fluoro-phenoxy)-benzenesulfonylamino]-tetrahydro-cyclopenta[1,3]dioxole-5-carboxylic acid hydroxyamide

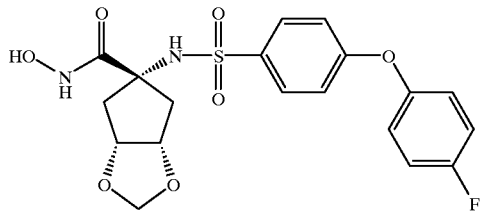

A) 1-[4-(4-Fluoro-phenoxy)-benzenesulfonylamino]-cyclopent-3-enecarboxylic acid ethyl ester To a stirred, cold (0° C.) solution of 1-aminocyclopent-3-ene-1-carboxylic acid ethyl ester (7.0 g, 45.1 mmol) (Park, K.-H.; Olmstead, M. M.; Kurth, M. J. J. Org. Chem. 1998, 63, 113–117 see also Kotha, S.; Sreenivasachary, N. Bioorg. Med. Chem. Lett. 1998, 8, 257–260.) in 150 mL of dichloromethane was added N,N-diisopropylethylamine (9.4 mL, 54.1 mmol). 4-(4-fluorophenoxy)benzenesulfonyl chloride was added in one portion followed by a catalytic amount (45 mg) of 4-(dimethylamino)pyridine. The ice bath was removed and the mixture was stirred for 48 h at 23° C. under a nitrogen atmosphere. The mixture was concentrated in vacuo, diluted with aqueous sodium bicarbonate, and extracted with ethyl acetate (2×). The combined organic extracts were washed with aqueous sodium bicarbonate (2×), dilute aqueous hydrochloric acid (2×), water (2×), brine (1×), dried (magnesium sulfate), filtered, and the filtrate was concentrated to give ca. 17 g of a brown oil. This oil was purified by flash chromatography, eluting with 3:1 hexanes/ethyl acetate to afford 9.9 g (54%) of 1-[4-(4-fluoro-phenoxy)-benzenesulfonylamino]-cyclopent-3-enecarboxylic acid ethyl ester as a yellow oil.

B) 1-[4-(4-Fluoro-phenoxy)-benzenesulfonylamino]-3,4-dihydroxy-cyclopentanecarboxylic acid ethyl ester To a vigorously stirred mixture of 1-[4-(4-fluoro-phenoxy)-benzenesulfonylamino]-cyclopent-3-enecarboxylic acid ethyl ester (6.3 g, 15.5 mmol) and 4-methylmorpholine N-oxide (3.8 g, 32.6 mmol) in 33 mL of tetrahydrofuran and 11 mL of water was added a solution of osmium tetroxide (0.196 M in tetrahydrofuran, 2.0 mL, 0.39 mmol) at 23° C. under a nitrogen atmosphere. The mixture was stirred for 2 h, diluted with aqueous sodium bisulfite, and stirred for an additional 2 minutes. The mixture was filtered through a cotton plug and was extracted with ethyl acetate (3×). The combined organic extracts were washed with aqueous sodium bisulfite (2×), water (2×), brine (1×), dried (sodium sulfate), filtered, and the filtrate was concentrated to give a yellow oil. This oil was purified by flash chromatography, eluting with 28:72 hexanes/ethyl acetate to afford 5.65 g (82%) of 1-[4-(4-fluoro-phenoxy)-benzenesulfonylamino]-3,4-dihydroxy-cyclopentanecarboxylic acid ethyl ester as a white foam (diastereomeric ratio of diols ca. 1.3:1; $^1$H NMR dmso-d$_6$).

C) A stirred solution of 1-[4-(4-fluoro-phenoxy)-benzenesulfonylamino]-3,4-dihydroxy-cyclopentanecarboxylic acid ethyl ester (mixture of diastereomers; 5.6 g, 12.8 mmol) and p-toluenesulfonic acid monohydrate (100 mg) in 100 mL of benzene and 50 mL of tetrahydrofuran was heated at reflux under a nitrogen atmosphere (interposed between the reaction vessel and the reflux condenser was a Dean-Stark trap charged with 4 angstrom molecular sieves). After 2 h an additional 300 mg of p-toluenesulfonic acid monohydrate was added. After a further 4 h the mixture was concentrated in vacuo (to remove the tetrahydrofuran). The residue was taken-up in 150 mL of benzene; an additional 400 mg of p-toluenesulfonic acid monohydrate was added and the mixture was heated at reflux for 17 h. The mixture was cooled to 23° C., diluted with aqueous sodium bicarbonate, and extracted with ethyl acetate (3×). The combined organic extracts were washed with aqueous sodium bicarbonate (2×), water (1×), brine (1×), dried (sodium sulfate), filtered, and the filtrate was concentrated to give a yellow oil. This oil was purified by flash chromatography, eluting with 35:65 hexanes/ethyl acetate to afford after a second purification of the mixed fractions 1.8 g (36%) of the lactone and 1.18 (21%) grams of the diol [1α,3αR,4αS]-1-[4-(4-fluoro-phenoxy)-benzenesulfonylamino]-3,4-dihydroxy-cyclopentanecarboxylic acid ethyl ester.

D) [3aR-(3aβ,5α,6aβ]-5-[4-(4-Fluoro-phenoxy)-benzenesulfonylamino]-tetrahydro-cyclopenta[1,3]dioxole-5-carboxylic acid ethyl ester A stirred mixture of [1α,3αR,4αS]-1-[4-(4-fluoro-phenoxy)-benzenesulfonylamino]-3,4-dihydroxy-cyclopentanecarboxylic acid ethyl ester (600 mg, 1.37 mmol), Amberlyst-15® (136 mg), and dimethoxymethane (0.6 mL, 6.83 mmol) in 27 mL of dichloromethane was heated at reflux for 4 h under a nitrogen atmosphere (interposed between the reaction vessel and the reflux condenser was a Dean-Stark trap charged with 4 angstrom molecular sieves). The mixture was cooled to 23° C., filtered, concentrated in vacuo, and the clear residue was purified by flash chromatography (elution with 55:45 hexanes/ethyl acetate) to afford 500 mg (81%) of [3aR-(3aβ,5α,6aβ]-5-[4-(4-fluoro-phenoxy)-benzenesulfonylamino]-tetrahydro-cyclopenta[1,3]dioxole-5-carboxylic acid ethyl ester as white foam.

Alternatively, a stirred solution of the diastereomeric diol mixture of 1-[4-(4-fluoro-phenoxy)-benzenesulfonylamino]-3,4-dihydroxy-cyclopentanecarboxylic acid ethyl ester (2.1 g, 4.78 mmol), dimethoxymethane (2.1 mL, 23.89 mmol), and a catalytic amount (50 mg) of p-toluenesulfonic acid monohydrate in 15 mL of dichloromethane was heated at 40° C. for 20 h under a nitrogen atmosphere. An additional 50 mg of p-toluenesulfonic acid monohydrate and 4 mL of dimethoxymethane was added. A Dean-Stark trap charged with 4 angstrom sieves was interposed between the reaction vessel and the reflux condenser and the mixture was heated at reflux for 20 h. The mixture was cooled to 22° C., diluted with aqueous sodium bicarbonate, and extracted with ethyl acetate (3x). The combined organic extracts were washed with aqueous sodium bicarbonate (1x), dilute aqueous hydrochloric acid (2x), water (2x), brine (1x), dried (magnesium sulfate), filtered, and the filtrate was concentrated to give a brown solid. This material was suspended in ethyl acetate, precipitating [3aS-(3aα,5α,6aα]-5-[4-(4-fluoro-phenoxy)-benzenesulfonylamino]-tetrahydro-cyclopenta[1,3]dioxole-5-carboxylic acid ethyl ester. Filtration, and collection of the solids gave 600 mg (27%) of [3aS-(3aα,5α,6aα]-5-[4-(4-fluoro-phenoxy)-benzenesulfonylamino]-tetrahydro-cyclopenta[1,3]dioxole-5-carboxylic acid ethyl ester as a white solid.

E) [3aR-(3aβ,5α,6aβ]-5-[4-(4-Fluoro-phenoxy)-benzenesulfonylamino]-tetrahydro-cyclopenta[1,3]dioxole-5-carboxylic acid A stirred solution of [3aR-(3aβ,5α,6aβ]-5-[4-(4-fluoro-phenoxy)-benzenesulfonylamino]-tetrahydro-cyclopenta[1,3]dioxole-5-carboxylic acid ethyl ester (500 mg, 1.1 mmol) and lithium hydroxide monohydrate (186 mg, 4.4 mmol) in 17 ml of tetrahydrofuran, 9 mL of methanol, and 20 mL of water was heated at 60° C. for 15.5 h under a nitrogen atmosphere. The reaction mixture was cooled to 23° C., diluted with water, and the pH was adjusted to 3.5 with aqueous hydrochloric acid. The mixture was extracted with ethyl acetate (3x) and the combined organic extracts were dried (sodium sulfate), filtered, and the filtrate was concentrated to give 449 mg (96%) of [3aR-(3aβ,5α,6aβ]-5-[4-(4-fluoro-phenoxy)-benzenesulfonylamino]-tetrahydro-cyclopenta[1,3]dioxole-5-carboxylic acid as a white foam. This material was used in the subsequent step without purification.

F) [3aR-(3aβ,5α,6aβ]-5-[4-(4-Fluoro-phenoxy)-benzenesulfonylamino]-tetrahydro-cyclopenta[1,3]dioxole-5-carboxylic acid hydroxyamide To a stirred, cold (0° C.) solution of [3aR-(3aβ,5α,6aβ]-5-[4-(4-fluoro-phenoxy)-benzenesulfonylamino]-tetrahydro-cyclopenta[1,3]dioxole-5-carboxylic acid (442 mg, 0.98 mmol) in 5 mL of dichloromethane was added a catalytic amount of N,N-dimethylformamide (16 μL) and oxalyl chloride (109 μL, 1.2 mmol) under a nitrogen atmosphere. The mixture was stirred for 7 h at 23° C. Meanwhile, pyridine (0.84 mL, 10 mmol) followed by trimethylsilyl chloride (0.6 mL, 5.0 mmol) was added to a cold (0° C.) flask charged with hydroxylamine hydrochloride (145 mg, 2.0 mmol) under a nitrogen atmosphere. The cold bath was removed and the mixture was stirred for 7 h at 23° C.

Both reaction vessels were cooled to 0° C. and the solution of the acid chloride was added to the stirred suspension of the N,O-bistrimethylsilylhydroxylamine via syringe. The cold bath was removed and the mixture was stirred for 20 h at 23° C. The reaction mixture was diluted with water and extracted with ethyl acetate (3x). The combined organic extracts were washed with water (2x), dried (sodium sulfate), filtered, and the filtrate was concentrated to give a pale yellow solid. This solid was stirred as a suspension in chloroform and diethyl ether. Filtration, collection, and drying of the solids gave 331 mg (77%) of [3aR-(3aβ,5α,6aβ]-5-[4-(4-fluoro-phenoxy)-benzenesulfonylamino]-tetrahydro-cyclopenta[1,3]dioxole-5-carboxylic acid hydroxyamide as a white solid.

M.p. 182–183° C. MS: m/z 439 (M+1). $^1$H NMR (dmso-d$_6$): d 10.40 (s, 1 H), 8.80 (s, 1 H), 7.98 (s, 1 H), 7.78 (d, J=8.9 Hz, 2H), 7.08–7.35 (m, 6H), 4.79 (s, 1H), 4.41 (br s, 2H), 2.33–2.40 (m, 2H), 1.68–1.74 (m, 2H).

EXAMPLE 2

[3aS-(3aα,5α,6aα]-5-[4-(4-Fluoro-phenoxy)-benzenesulfonylamino]-tetrahydro-cyclopenta[1,3]dioxole-5-carboxylic acid hydroxamide

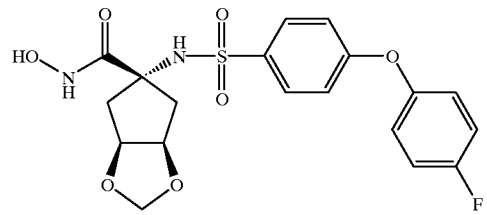

This compound was prepared according to the same procedure as Example 1, starting with [3aS-(3aα,5α,6aα]-5-[4-(4-fluoro-phenoxy)-benzenesulfonylamino]-tetrahydro-cyclopenta[1,3]dioxole-5-carboxylic acid ethyl ester obtained in step D. Alternatively, the synthesis can use the [1α,3βS,4βR]-1-[4-(4-fluoro-phenoxy)-benzenesulfonylamino]-3,4-dihydroxy-cyclopentanecarboxylic acid ethyl ester diol isomer obtained in pure form by crystallization in step B.

M.p. 146–149° C. MS: m/z 437 (M–1). $^1$H NMR (dmso-d$_6$): d 10.38 (s, 1 H), 8.75 (s, 1 H), 7.88 (s, 1 H), 7.73 (d, J=8.9 Hz, 2H), 7.04–7.28 (m, 6H), 4.83 (s, 1H), 4.10 (br s, 2H), 2.29–2.33 (m, 2H), 1.76–1.80 (m, 2H).

EXAMPLE 3

[3aR-(3aβ,5α,6aβ)]-5-[4-(4-Chloro-phenoxy)-benzenesulfonylamino]-tetrahydro-cyclopenta[1,3]dioxole-5-carboxylic acid hydroxyamide

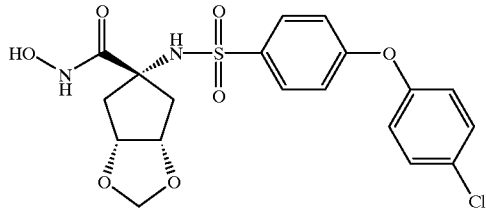

This compound was prepared according to the same procedure as Example 1, starting with 4-(4-chlorophenoxy)benzenesulfonyl chloride in step A. The requisite [1α,3αR,4αS]-1-[4-(4-chloro-phenoxy)-benzenesulfonyamino]-3,4-dihydroxy-cyclopentanecarboxylic acid ethyl ester diol isomer was obtained by lactonization of a diol mixture (step C) and chromatographic isolation of the remaining diol isomer.

MS: m/z 453 (M−1).

EXAMPLE 4

[3aS-(3aα,5α,6aα)]-5-[4-(4-Chloro-phenoxy)-benzenesulfonylamino]-tetrahydro-cyclopenta[1,3]dioxole-5-carboxylic acid hydroxyamide

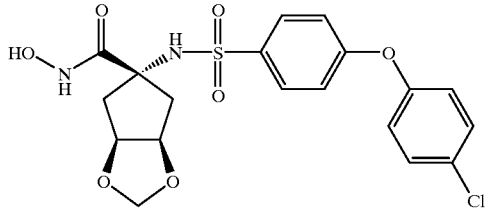

This compound was prepared in an analogous manner to Example 2, starting with 4-(4-chlorophenoxy)benzenesulfonyl chloride in step A. The requisite [1α,3βS,4βR]-1-[4-(4-chloro-phenoxy)-benzenesulfonylamino]-3,4-dihydroxy-cyclopentanecarboxylic acid ethyl ester diol isomer crystallized out in pure form in step B.

MS: m/z 455 (M+1).

EXAMPLE 5

[3aR-(3aβ,5α,6aβ)]-5-[4-(4-Fluoro-phenoxy)-benzenesulfonylamino]-2-oxo-tetrahydro-cyclopenta[1,3]dioxole-5-carboxylic acid hydroxyamide

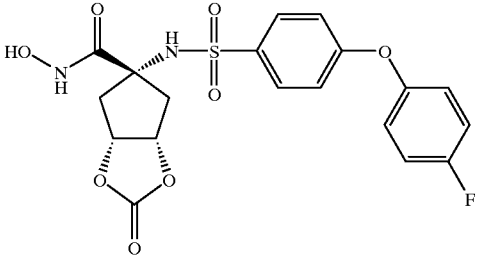

A) [1α,3αR,4αS]-1-[4-(4-fluoro-phenoxy)-benzenesulfonylamino]-3,4-dihydroxy-cyclopentanecarboxylic acid To a stirred solution of [1α,3αR,4αS]-1-[4-(4-fluoro-phenoxy)-benzenesulfonylamino]-3,4-dihydroxy-cyclopentanecarboxylic acid ethyl ester (570 mg, 1.3 mmol; prepared according to the same procedure as Example 1 steps A and B), in tetrahydrofuran (17 mL), was added lithium hydroxide monohydrate (217 mg, 5.2 mmols), methanol (9 mL), and water (20 mL). The resulting mixture was heated to 60° C. for 4 hours. The reaction mixture was added to dilute aqueous hydrochloric acid. The pH was adjusted to 2.5 using 1 N aqueous hydrogen chloride and the mixture was extracted with ethyl acetate (3×). The combined organic extracts were dried over sodium sulfate, filtered, and the filtrate was concentrated to afford [1α,3αR,4αS]-1-[4-(4-fluoro-phenoxy)-benzenesulfonylamino]-3,4-dihydroxy-cyclopentanecarboxylic acid as a solid, which was used in the subsequent step without purification.

B) [3aR-(3aβ,5α,6aβ)]-5-[4-(4-Fluoro-phenoxy)-benzenesulfonylamino]-2-oxo-tetrahydro-cyclopenta[1,3]dioxole-5-carboxylic acid To a stirred, cold (0° C.) solution of [1α,3αR,4αS]-1-[4-(4-fluoro-phenoxy)-benzenesulfonylamino]-3,4-dihydroxy-cyclopentanecarboxylic acid (428 mg, 100 μmol) in methylene chloride (10 mL) was added 1,1'-carbonyldiimidazole (169 mg, 100 μmol). The ice bath was removed 45 minutes later. The suspension was stirred under an nitrogen atmosphere at ambient temperature (23° C.) for 72 hours. The reaction was quenched with water and the aqueous layer was separated. The aqueous layer was acidified to pH of 4 using 1 N hydrogen chloride and extracted with ethyl acetate (3×). The combined organic extracts were dried over sodium sulfate, filtered, and the filtrate was concentrated. The resulting crude material was purified by silica gel chromatography (elution with 85:15 methylene chloride/methanol and 1% acetic acid) to afford [3aR-(3aβ,5α,6aβ)]-5-[4-(4-fluoro-phenoxy)-benzenesulfonylamino]-2-oxo-tetrahydro-cyclopenta[1,3]dioxole-5-carboxylic acid as a solid.

C) [3aR-(3aβ,5α,6aβ)]-5-[4-(4-Fluoro-phenoxy)-benzenesulfonylamino]-2-oxo-tetrahydro-cyclopenta[1,3]dioxole-5-carboxylic acid hydroxyamide To a stirred, cold (0° C.) suspension of [3aR-(3aβ,5α,6aβ)]-5-[4-(4-fluoro-phenoxy)-benzenesulfonylamino]-2-oxo-tetrahydro-cyclopenta[1,3]dioxole-5-carboxylic acid (70 mg, 160 μmol) in methylene chloride (1 mL), was added oxalyl chloride (16 μL, 192 μmol) drop-wise while stirring under a nitrogen atmosphere. Mean while, chlorotrimethylsilane (91 μL, 720 μmol) was added drop-wise to a stirred, cold (0° C.) solution of hydroxylamine hydrochloride (22 mg, 320 μmol) in pyridine (129 μL, 1.6 mmol). Both reaction mixtures were warmed to ambient temperature (23° C). After 72 hours both reaction mixtures were cooled to 0° C. and the acid chloride solution was added to the stirred suspension of the bis-(trimethylsilyl)hydroxylamine via syringe. The resulting mixture was stirred at ambient temperature (23° C.) for 24 hours before 200 μL of 1 N aqueous hydrogen chloride was added. The reaction mixture was stirred for 7 hours when it was added to water and the aqueous phase was extracted with ethyl acetate (3×). The combined organic extracts were washed with water (2×), and brine (2×), and dried over sodium sulfate, filtered, and the filtrate was concentrated. The resulting crude material was suspended in diethyl ether and the mixture was stirred for 16 hours. Filtration and collection of the solids afforded 52 mg of [3aR-(3aβ,5α,6aβ]-5-[4-(4-fluoro-phenoxy)-benzenesulfonylamino]-2-oxo-tetrahydro-cyclopenta[1,3]dioxole-5-carboxylic acid hydroxyamide. MS: m/z 451 (M−1).

EXAMPLE 6

[3aS-(3aα,5α,6aα]-5-(4-Benzyloxy-benzenesulfonylamino)-tetrahydro-cyclopenta[1,3]dioxole-5-carboxylic acid hydroxyamide

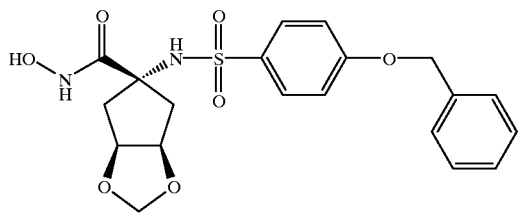

This compound was prepared in an analogous manner to Example 2, starting with 4-(4-benzyloxy)-benzenesulfonyl chloride in step A. The requisite [1α,3αS,4αR]-1-[4-(4-benzyloxy)-benzenesulfonylamino]-3,4-dihydroxy-cyclopentanecarboxylic acid ethyl ester diol isomer crystallized out in pure form in step B.

MS: m/z 435 (M+1).

EXAMPLE 7

[3aS-(3aα,5α,6aα]-5-[4-(4-Fluoro-benzyloxy-benzenesulfonylamino]-tetrahydro-cyclopenta[1,3]dioxole-5-carboxylic acid hydroxyamide

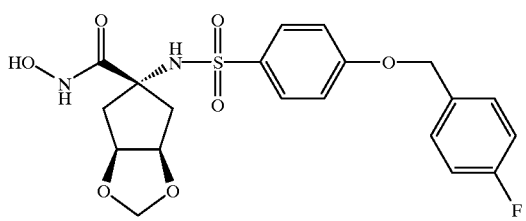

A) [3aS-(3aα,5α,6aα]-5(4-Hydroxy-benzenesulfonylamino)-tetrahydro-cyclopenta[1,3]dioxole-5-carboxylic acid ethyl ester A mixture of [3aS-(3aα,5α,6aα]-5-(4-benzyloxy-benzenesulfonylamino)-tetrahydro-cyclopenta[1,3]dioxole-5-carboxylic acid ethyl ester (1.2 g, 2.7 mmol; obtained from step D of Example 6) and 10% palladium on carbon in methylene chloride and methanol was shaken for 3 hours under a 45 psi atmosphere of hydrogen gas. The resulting mixture was filtered through nylon, and the filtrate was concentrated in vacuo to give [3aS-(3aα,5α,6aα]-5-(4-hydroxy-benzenesulfonylamino)-tetrahydro-cyclopenta[1,3]dioxole-5-carboxylic acid ethyl ester.

B) [3aS-(3aα,5α,6aα]-5-[4-(4-Fluoro-benzyloxy)-benzenesulfonylamino]-tetrahydro-cyclopenta[1,3]dioxole-5-carboxylic acid ethyl ester To a stirred solution of [3aS-(3aα,5α,6aα]-5-(4-hydroxy-benzenesulfonylamino)-tetrahydro-cyclopenta[1,3]dioxole-5-carboxylic acid ethyl ester (431 mg, 1.2 mmol) in dimethylformamide (6 mL) was added cesium carbonate (432 mg, 1.3 mmol) followed by 4-fluorobenzylbromide (165 μL, 1.3 mmol). The suspension was stirred at ambient temperature (23° C.) while under a nitrogen atmosphere for 19 hours. The resulting material was added to water, and the aqueous phase was extracted with ethyl acetate (3×). The combined organic extracts were dried over sodium sulfate, filtered, and the filtrate was concentrated. The residue was crystallized using chloroform and ethyl acetate to afford [3aS-(3aα,5α,6aα]-5-[4-(4-fluoro-benzyloxy)-benzenesulfonylamino]-tetrahydro-cyclopenta[1,3]dioxole-5-carboxylic acid ethyl ester as white crystals.

C) [3aS-(3aα,5α,6aα]-5-[4-(4-Fluoro-benzyloxy)-benzenesulfonylamino]-tetrahydro-cyclopenta[1,3]dioxole-5-carboxylic acid A solution of [3aS-(3aα,5α,6aα]-5-[4-(4-fluoro-benzyloxy)-benzenesulfonylamino]-tetrahydro-cyclopenta[1,3]dioxole-5-carboxylic acid ethyl ester (360 mg, 770 μmol) tetrahydrofuran (10 mL), lithium hydroxide monohydrate (130 mg, 3.1 mmol), methanol (8 mL) and water (13 mL) was heated to 60 ° C. for 4 hours. The aqueous layer was acidified to a pH of 3.5 using 1N aqueous hydrogen chloride and the mixture was extracted with ethyl acetate (3×). The combined organic extracts were dried over sodium sulfate, filtered, and the filtrate was concentrated to afford [3aS-(3aα,5α,6aα]-5-[4-(4-fluoro-benzyloxy)-benzenesulfonylamino]-tetrahydro-cyclopenta[1,3]dioxole-5-carboxylic acid.

D) [3aS-(3aα,5α,6aα]-5-[4-(4-Fluoro-benzyloxy)-benzenesulfonylamino]-tetrahydro-cyclopenta[1,3]dioxole-5-carboxylic acid hydroxyamide To a stirred, cold (0° C.) suspension of [3aS-(3aα,5α,6aα]-5-[4-(4-fluoro-benzyloxy)-benzenesulfonylamino]-tetrahydro-cyclopenta[1,3]dioxole-5-carboxylic acid (336 mg, 768 μmol) in methylene chloride (4 mL), was added dimethylformamide (50 μL) followed by oxalyl chloride (80 μL, 920 μmol) drop-wise under a nitrogen atmosphere. Mean while, chlorotrimethylsilane (430 μL, 3.4 mmol) was added drop-wise to a stirred, cold (0° C.) solution of hydroxylamine hydrochloride (106 mg, 1.5 mmol) in pyridine (620 μL, 7.7 mmol). Both reaction mixtures were warmed to ambient temperature (23° C.). After 24 hours both reaction mixtures were cooled to 0° C. and the acid chloride solution was added to the stirred suspension of the bis-(trimethylsilyl)hydroxylamine via cannula. The resulting mixture was stirred at ambient temperature (23° C.) for 48 hours before 2 mL of 1 N aqueous hydrogen chloride was added. The reaction mixture stirred for 2 hours when it was added to water and the aqueous phase was extracted with ethyl acetate. The combined organic extracts were washed with water and brine, dried over sodium sulfate, filtered, and the filtrate was concentrated. The resulting crude material was suspended in diethyl ether and trace amounts of chloroform and hexanes and the mixture was stirred for 16 hours. Filtration and collection of the solids afforded 285 mg of [3aS-(3aα,5α,6aα]-5-[4-(4-Fluoro-benzyloxy)-benzenesulfonylamino]-tetrahydro-cyclopenta[1,3]dioxole-5-carboxylic acid hydroxyamide:

MS: m/z 453 (M+1).

EXAMPLE 8

[3aS-(3aα,5α,6aα]-5-[4-(2,5-Difluoro-benzyloxy)-benzenesulfonylamino]-tetrahydro-cyclopenta[1,3] dioxole-5-carboxylic acid hydroxyamide This compound was prepared in an analogous manner to Example 7, except that 2,5-difluorobenzyl bromide was used in step B.

MS: m/z 469 (M−1).

What is claimed is:

1. A compound of the formula

I wherein

X is >$CR^3R^4$ or >C=O;

Z is >$CH_2$ or >$NR^1$;

$R^1$ is hydrogen, $(C_1-C_6)$alkyl, $(C_6-C_{10})$aryl$(C_1-C_6)$alkyl, $(C_2-C_9)$heteroaryl$(C_1-C_6)$alkyl or a group of the formula $$-(CH_2)_n-\overset{O}{\underset{}{C}}-OR^2;$$

n is an integer from one to six;

$R^2$ is hydrogen or $(C_1-C_6)$alkyl;

$R^3$ is hydrogen or $(C_1-C_6)$alkyl;

$R^4$ is hydrogen, $(C_1-C_6)$alkyl, $(C_1-C_6)$alkoxy$(C_1-C_6)$ alkyl, $(C_6-C_{10})$aryl, $(C_2-C_9)$heteroaryl, $(C_6-C_{10})$aryl $(C_1-C_6)$alkyl, $(C_6-C_{10})$aryl$(C_6-C_{10})$aryl, $(C_6-C_{10})$aryl $(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl $(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy $(C_2-C_9)$heteroaryl, $(C_2-C_9)$heteroaryloxy$(C_1-C_6)$ alkyl, $(C_2-C_9)$heteroaryloxy$(C_6-C_{10})$aryl, $(C_2-C_9)$ heteroaryloxy$(C_2-C_9)$heteroaryl, $(C_6-C_{10})$aryl$(C_1-C_6)$ alkyl$(C_6-C_{10})$aryl, $(C_6-C_{10})$aryl$(C_1-C_6)$alkyl$(C_2-C_9)$ heteroaryl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_6-C_{10})$aryloxy$(C_1-C_6)$alkyl$(C_6-C_{10})$aryl, $(C_6-C_{10})$ aryloxy$(C_1-C_6)$alkyl$(C_2-C_9)$heteroaryl, $(C_2-C_9)$ heteroaryl$(C_1-C_6)$alkyl$(C_6-C_{10})$aryl, $(C_2-C_9)$ heteroaryl$(C_1-C_6)$alkyl$(C_2-C_9)$heteroaryl, $(C_2-C_9)$ heteroaryl$(C_1-C_6)$alkoxy$(C_6-C_{10})$aryl, $(C_2-C_9)$ heteroaryl$(C_1-C_6)$alkoxy$(C_2-C_9)$heteroaryl, $(C_2-C_9)$ heteroaryloxy$(C_1-C_6)$alkyl$(C_6-C_{10})$aryl, $(C_2-C_9)$ heteroaryloxy$(C_1-C_6)$alkyl$(C_2-C_9)$heteroaryl, $(C_6-C_{10})$aryl$(C_6-C_{10})$aryl$(C_1-C_6)$alkyl or $(C_6-C_{10})$ aryl$(C_1-C_6)$alkoxy$(C_1-C_6)$alkyl, wherein each of said $(C_6-C_{10})$aryl or $(C_2-C_9)$heteroaryl moieties is optionally substituted on any of the ring carbon atoms capable of forming an additional bond by one or more substituents per ring, independently selected from fluoro, chloro, bromo, $(C_1-C_6)$alkyl, $(C_1-C_6)$alkoxy, perfluoro $(C_1-C_3)$alkyl, perfluoro$(C_1-C_3)$alkoxy and $(C_6-C_{10})$ aryloxy;

Q is $(C_1-C_6)$alkyl, $(C_6-C_{10})$aryl, $(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_2-C_9)$heteroaryl $(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryloxy $(C_1-C_6)$alkyl, $(C_6-C_{10})$aryloxy$(C_6-C_{10})$aryl, $(C_6-C_{10})$ aryloxy$(C_2-C_9)$heteroaryl, $(C_2-C_9)$heteroaryloxy $(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_6-C_{10})$aryl $(C_1-C_6)$alkyl$(C_6-C_{10})$aryl, $(C_6-C_{10})$aryl$(C_1-C_6)$alkyl $(C_2-C_9)$heteroaryl, $(C_6-C_{10})$aryl$(C_1-C_6)$alkoxy $(C_6-C_{10})$aryl, $(C_6-C_{10})$aryl$(C_1-C_6)$alkoxy$(C_2-C_9)$ heteroaryl, $(C_6-C_{10})$aryloxy$(C_1-C_6)$alkyl$(C_6-C_{10})$aryl, $(C_6-C_{10})$aryloxy$(C_1-C_6)$alkyl$(C_2-C_9)$heteroaryl, $(C_2-C_9)$heteroaryl$(C_1-C_6)$alkyl$(C_6-C_{10})$aryl, $(C_2-C_9)$ heteroaryl$(C_1-C_6)$alkyl$(C_2-C_9)$heteroaryl, $(C_2-C_9)$ heteroaryl$(C_1-C_6)$alkoxy$(C_6-C_{10})$aryl, $(C_2-C_9)$ heteroaryl$(C_1-C_6)$alkoxy$(C_2-C_9)$heteroaryl, $(C_2-C_9)$ heteroaryloxy$(C_1-C_6)$alkyl$(C_6-C_{10})$aryl, $(C_2-C_9)$ heteroaryloxy$(C_1-C_6)$alkyl$(C_2-C_9)$heteroaryl, $(C_6-C_{10})$aryl$(C_6-C_{10})$aryl$(C_1-C_6)$alkyl or $(C_6-C_{10})$ aryl$(C_1-C_6)$alkoxy$(C_1-C_6)$alkyl, wherein each of said $(C_6-C_{10})$aryl or $(C_2-C_9)$heteroaryl moieties is optionally substituted on any of the ring carbon atoms capable of forming an additional bond by one or more substituents per ring, independently selected from fluoro, chloro, bromo, $(C_1-C_6)$alkyl, $(C_1-C_6)$alkoxy, perfluoro $(C_1-C_3)$alkyl, perfluoro$(C_1-C_3)$alkoxy and $(C_6-C_{10})$ aryloxy;

with the proviso that when X is >C=O and Z is $NR^1$ then $R^1$ must be hydrogen, $(C_1-C_6)$alkyl, $(C_6-C_{10})$aryl $(C_1-C_6)$alkyl or $(C_2-C_9)$heteroaryl $(C_1-C_6)$alkyl;

or a pharmaceutically acceptable salt thereof.

2. A compound according to claim 1, wherein Z is —$CH_2$—.

3. A compound according to claim 1, wherein X is —$CH_2$—.

4. A compound according to claim 1, wherein X is >C=O.

5. A compound according to claim 1, wherein X is >$CR^3R^4$.

6. A compound according to claim 1, wherein X is —$CH_2$— and Z is —$CH_2$—.

7. A compound according to claim 1, wherein X is >C=O and Z is —CH$_2$—.

8. A compound according to claim 1, wherein X is >CR$^3$R$^4$ and Z is —CH$_2$—.

9. A compound according to claim 1, wherein Z is >NR$^1$.

10. A compound according to claim 8, wherein R$^1$ is hydrogen, (C$_1$–C$_6$)alkyl, (C$_6$–C$_{10}$)aryl(C$_1$–C$_6$)alkyl or (C$_2$–C$_9$)heteroaryl(C$_1$–C$_6$)alkyl.

11. A compound according to claim 9, wherein X is —CH$_2$—.

12. A compound according to claim 10, wherein X is —CH$_2$—.

13. A compound according to claim 9, wherein X is >C=O.

14. A compound according to claim 10, wherein X is >C=O.

15. A compound according to claim 9, wherein X is >CR$^3$R$^4$.

16. A compound according to claim 10, wherein X is >CR$^3$R$^4$.

17. A compound according to claim 1, wherein Q is optionally substituted (C$_6$–C$_{10}$)aryl, (C$_6$–C$_{10}$)aryloxy (C$_6$–C$_{10}$)aryl, (C$_2$–C$_9$)heteroaryloxy(C$_6$–C$_{10}$)aryl or (C$_6$–C$_{10}$)aryl(C$_1$–C$_6$)alkoxy(C$_6$–C$_{10}$)aryl.

18. A compound according to claim 1, wherein Q is optionally substituted (C$_6$–C$_{10}$)aryloxy(C$_6$–C$_{10}$)aryl.

19. A compound according to claim 1, wherein Q is optionally substituted (C$_2$–C$_9$)heteroaryloxy(C$_6$–C$_{10}$)aryl.

20. A compound according to claim 1, wherein Q is optionally substituted (C$_6$–C$_{10}$)aryl(C$_1$–C$_6$)alkoxy(C$_6$–C$_{10}$)aryl.

21. A compound according to claim 9, wherein Q is optionally substituted (C$_6$–C$_{10}$)aryl, (C$_6$–C$_{10}$)aryloxy (C$_6$–C$_{10}$)aryl, (C$_2$–C$_9$)heteroaryloxy(C$_6$–C$_{10}$)aryl, or (C$_6$–C$_{10}$)aryl(C$_1$–C$_6$)alkoxy(C$_6$–C$_{10}$)aryl.

22. A compound according to claim 9, wherein Q is optionally substituted (C$_6$–C$_{10}$)aryloxy(C$_6$–C$_{10}$)aryl.

23. A compound according to claim 9, wherein Q is optionally substituted (C$_2$–C$_9$)heteroaryloxy(C$_6$–C$_{10}$)aryl.

24. A compound according to claim 9, wherein Q is optionally substituted (C$_6$–C$_{10}$)aryl(C$_1$–C$_6$)alkoxy(C$_6$–C$_{10}$)aryl.

25. A compound according to claim 15, wherein said Q optional substituent is hydrogen, fluoro, chloro, (C$_1$–C$_6$)alkyl or (C$_1$–C$_6$)alkoxy.

26. A compound according to claim 15, wherein said Q optional substituent is in the para position of the terminal ring.

27. A compound according to claim 15, wherein said Q optional substituent is in the ortho position of the terminal ring.

28. A compound according to claim 1, wherein said compound is selected from the group consisting of:

[3aR-(3aβ,5α,6aβ]-5-[4-(4-fluoro-phenoxy)-benzenesulfonylamino]-tetrahydro-cyclopenta[1,3]dioxole-5-carboxylic acid hydroxyamide,

[3aS-(3aα,5α,6aα]-5-[4-(4-fluoro-phenoxy)-benzenesulfonylamino]-tetrahydro-cyclopenta[1,3]dioxole-5-carboxylic acid hydroxyamide,

[3aR-(3aβ,5α,6aβ]-5-[4-(4-chloro-phenoxy)-benzenesulfonylamino]-tetrahydro-cyclopenta[1,3]dioxole-5-carboxylic acid hydroxyamide and

[3aS-(3aα,5α,6aα]-5-[4-(4-chloro-phenoxy)-benzenesulfonylamino]-tetrahydro-cyclopenta[1,3]dioxole-5-carboxylic acid hydroxyamide,

[3aR-(3aβ,5α,6aβ]-5-[4-(4-Fluoro-phenoxy)-benzenesulfonylamino]-2-oxo-tetrahydro-cyclopenta[1,3]dioxole-5-carboxylic acid hydroxyamide,

[3aS-(3aα,5α,6aα]-5-(4-Benzyloxy-benzenesulfonylamino)-tetrahydro-cyclopenta[1,3]dioxole-5-carboxylic acid hydroxyamide and

[3aS-(3aα,5α,6aα]-5-[4-(4-Fluoro-benzyloxy)-benzenesulfonylamino]-tetrahydro-cyclopenta[1,3]dioxole-5-carboxylic acid hydroxyamide.

29. A pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of claim 1 effective in such treatment and a pharmaceutically acceptable carrier.

30. A method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of claim 1, effective in treating such a condition.

31. A pharmaceutical composition for the treatment of a condition which can be treated by the inhibition of matrix metalloproteinases in a mammal, including a human, comprising an amount of a compound of claim 1 effective in such treatment and a pharmaceutically acceptable carrier.

32. A pharmaceutical composition for the treatment of a condition which can be treated by the inhibition of a mammalian reprolysin in a mammal, including a human, comprising an amount of a compound of claim 1 effective in such treatment and a pharmaceutically acceptable carrier.

33. A method for the inhibition of matrix metalloproteinases in a mammal, including a human, comprising administering to said mammal an effective amount of a compound of claim 1.

34. A method for the inhibition of a mammalian reprolysin in a mammal, including a human, comprising administering to said mammal an effective amount of a compound of claim 1.

* * * * *